US008349615B2

(12) United States Patent
Eckermann et al.

(10) Patent No.: US 8,349,615 B2
(45) Date of Patent: Jan. 8, 2013

(54) METHOD FOR THE OPTIMIZATION OF CHROMATOGRAPHIC PURIFICATION PROCESSES FOR BIOLOGICAL MOLECULES

(75) Inventors: Christian Eckermann, Biberach (DE); Sybille Ebert, Mittelbiberach (DE); Stefanie Rubenwolf, Nattenhausen (DE); Dorothee Ambrosius, Laupheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 939 days.

(21) Appl. No.: 11/762,119

(22) Filed: Jun. 13, 2007

(65) Prior Publication Data

US 2008/0066530 A1  Mar. 20, 2008

Related U.S. Application Data

(60) Provisional application No. 60/805,100, filed on Jun. 19, 2006.

(30) Foreign Application Priority Data

Jun. 14, 2006 (DE) .......................... 10 2006 027 496

(51) Int. Cl.
*G01N 30/02* (2006.01)
*G01N 30/38* (2006.01)
(52) U.S. Cl. .................. 436/161; 73/61.52; 210/656
(58) Field of Classification Search .................. 436/161; 422/70, 101; 73/61.52–61.58; 210/198.2, 210/656
See application file for complete search history.

(56) References Cited

U.S. PATENT DOCUMENTS

2005/0176937 A1  8/2005 Cramer
2006/0096924 A1*  5/2006 Schlueter ....................... 210/656

FOREIGN PATENT DOCUMENTS

DE        19860354 A1      6/2000
WO     2004028658 A1      4/2004
WO  WO 2004/028658  *    4/2004

OTHER PUBLICATIONS

Sheer et al, High Througput Sample preparation for Protein/Peptide Structural Characterization, Jul. 13, 1998, http://www.abrf.org/JBT/Articles/JBT0009/JBT0009.html.*
Bensch et al, Chem. Eng. Technol. vol. 28, No. 11, pp. 1274-1284, published online Nov. 7, 2005.*
International Search Report of corresponding PCT Application No. PCT/EP2007/055776 mailed on Oct. 2, 2007.
DE19860354; Publication Date: Jun. 29, 2000; Name of Patentee: Univ Dortmund; Display from INPADOCDB.
DE19860354; Publication Date: Jun. 29, 2000; Name of Patentee: Univ Dortmund; Machine Translation in English.

* cited by examiner

*Primary Examiner* — Jan Ludlow
(74) *Attorney, Agent, or Firm* — Michael P. Morris; Eduoard G. Lebel

(57) ABSTRACT

The invention relates to a method of finding suitable parameters for the chromatographic purification of biomolecules. The method consists of equilibration, charging, washing and eluting steps, this sequence of steps being carried out by the partial batch method. The parameters determined in small, preferably numerous parallel test batches provide conclusions as to the chromatography conditions under which a given biomolecule can be purified optimally by column chromatography, optionally even on a larger scale.

11 Claims, 19 Drawing Sheets

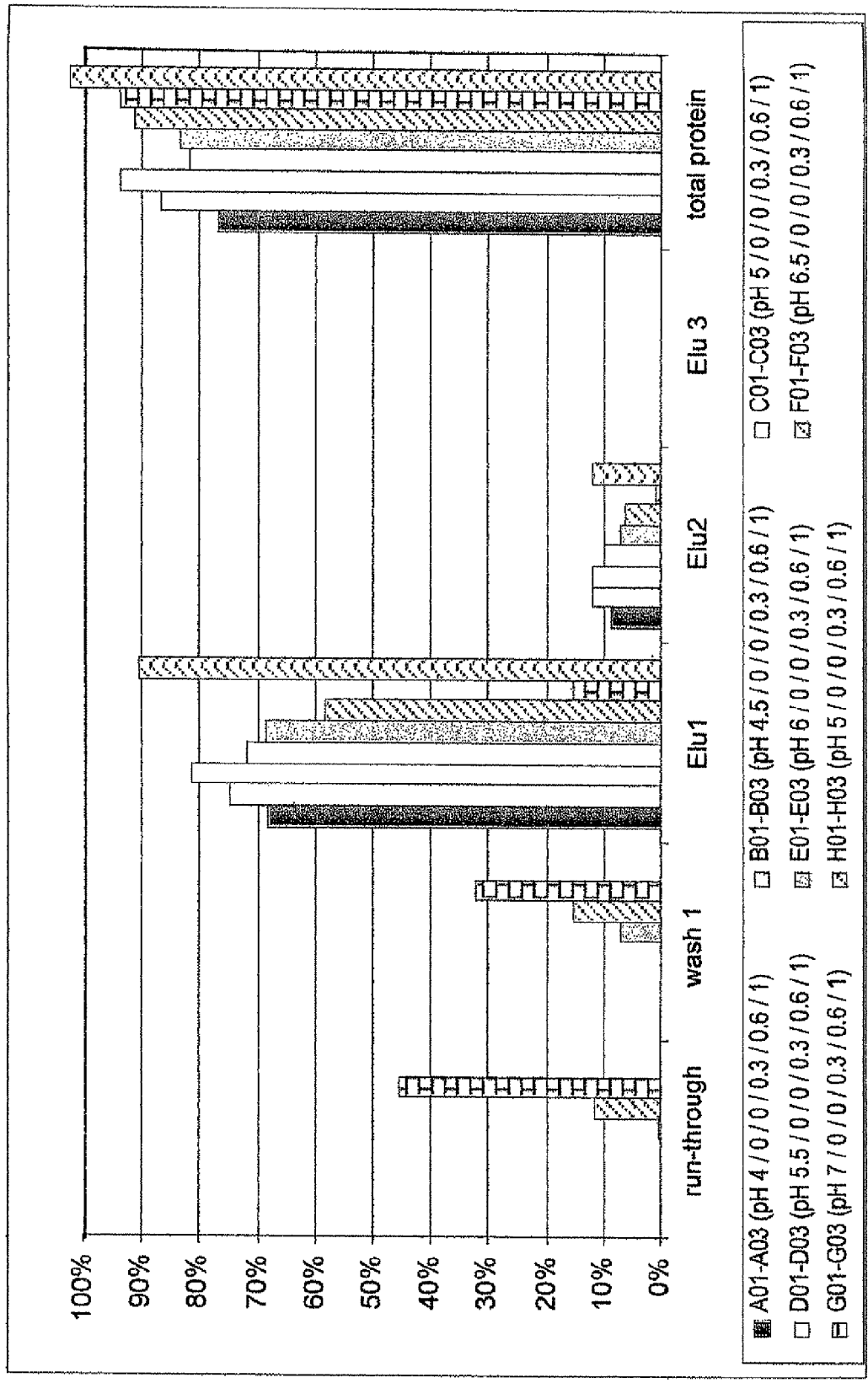
Fig. 3.1

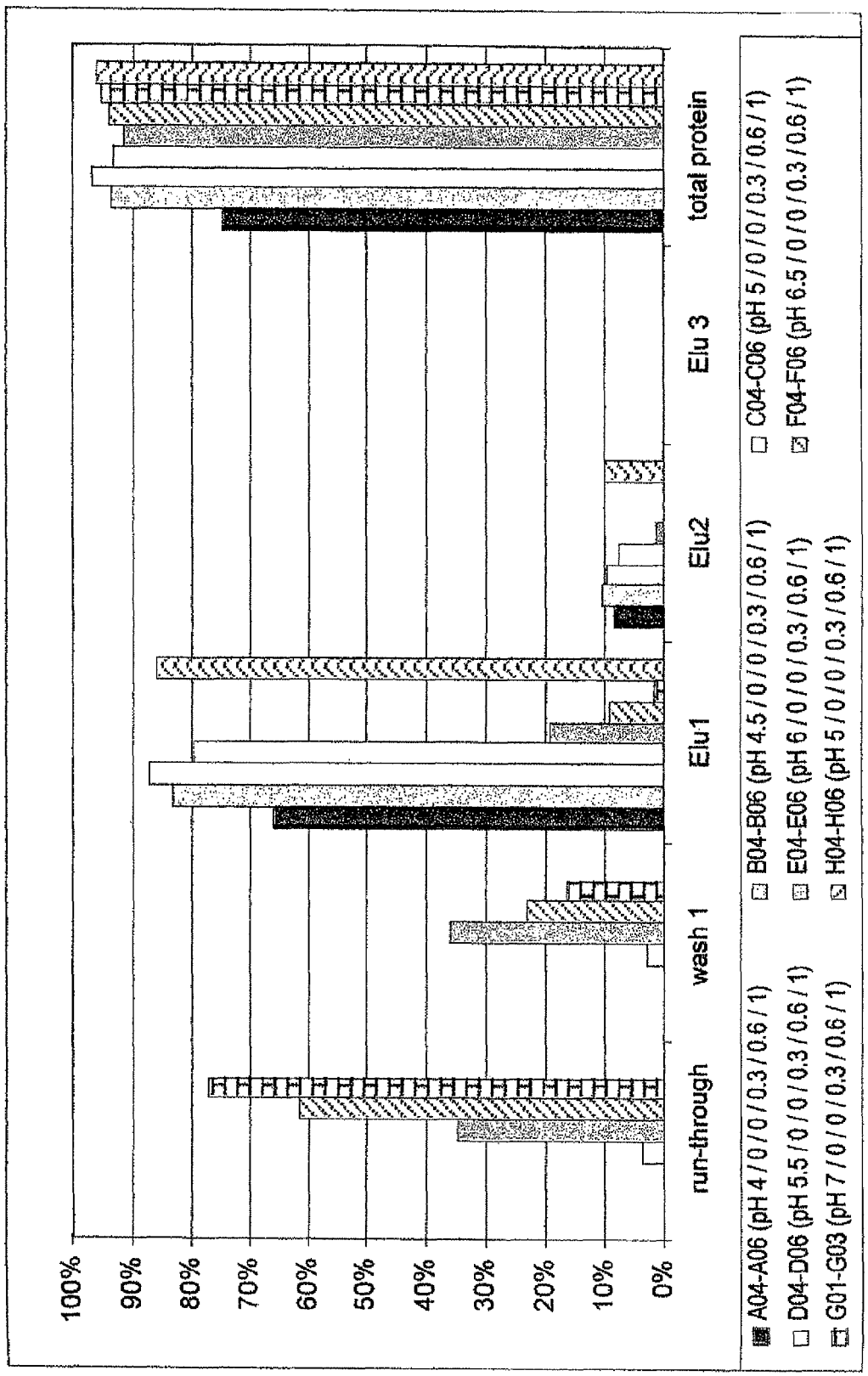
Fig. 3.2

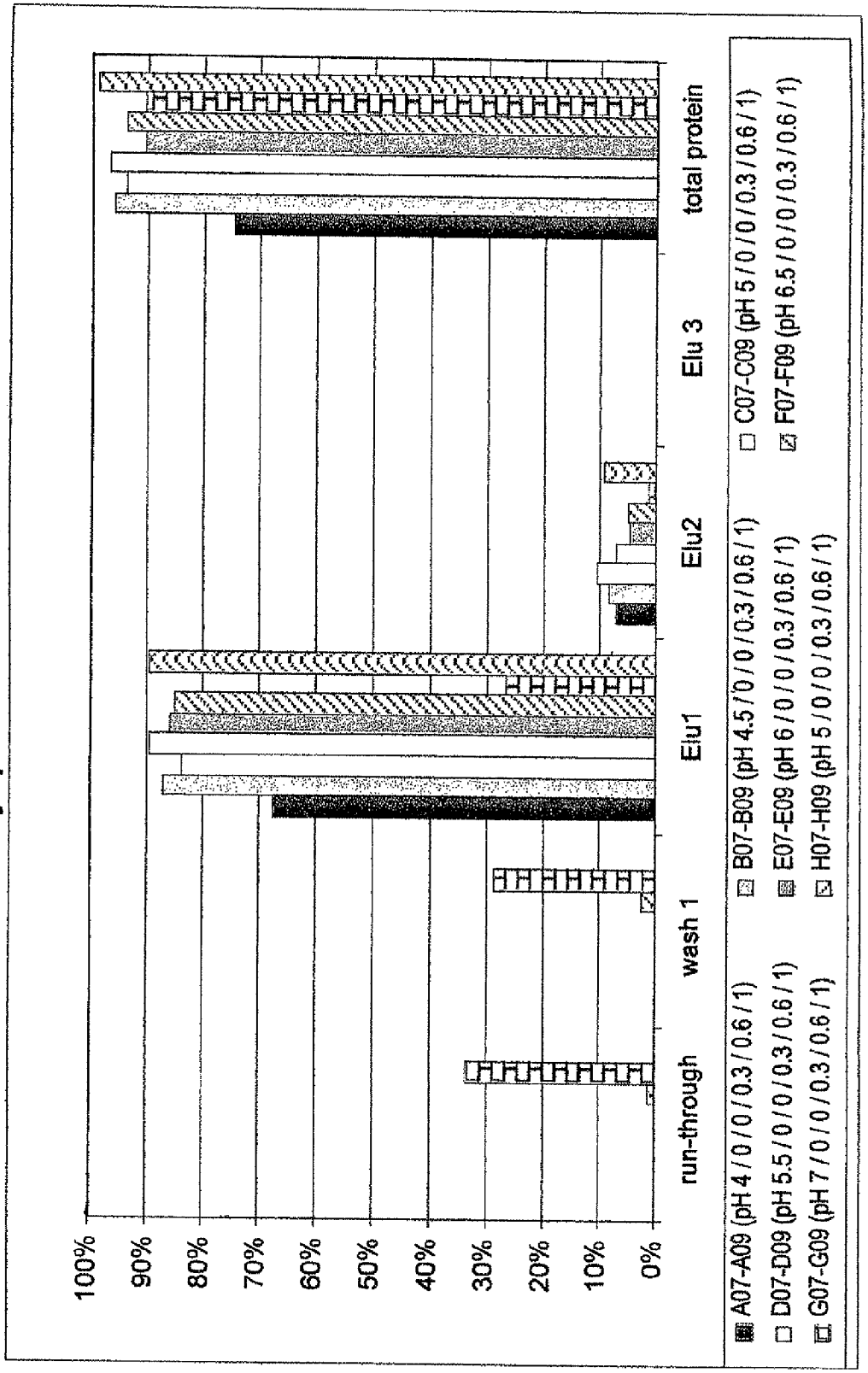

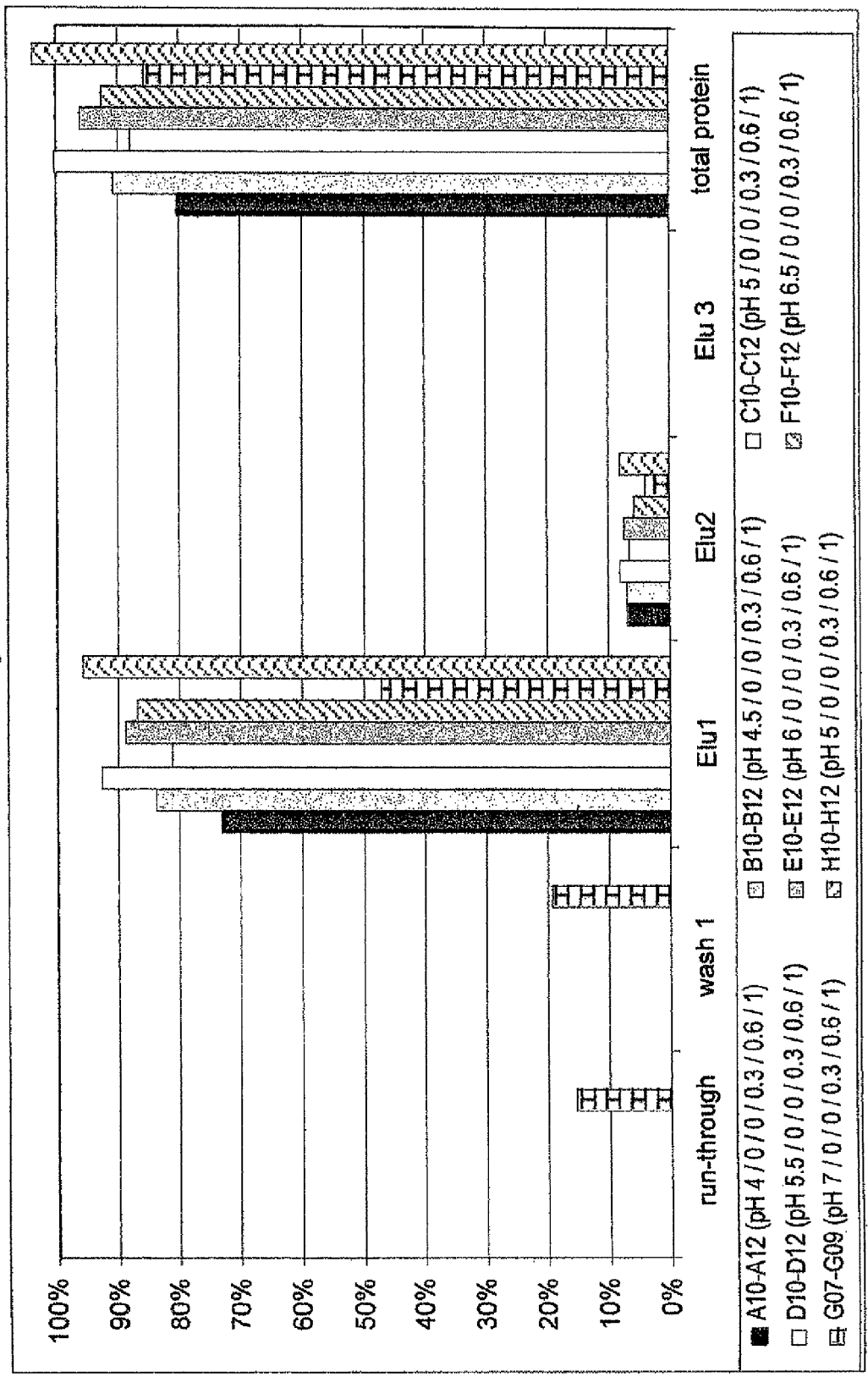
Fig. 3.4

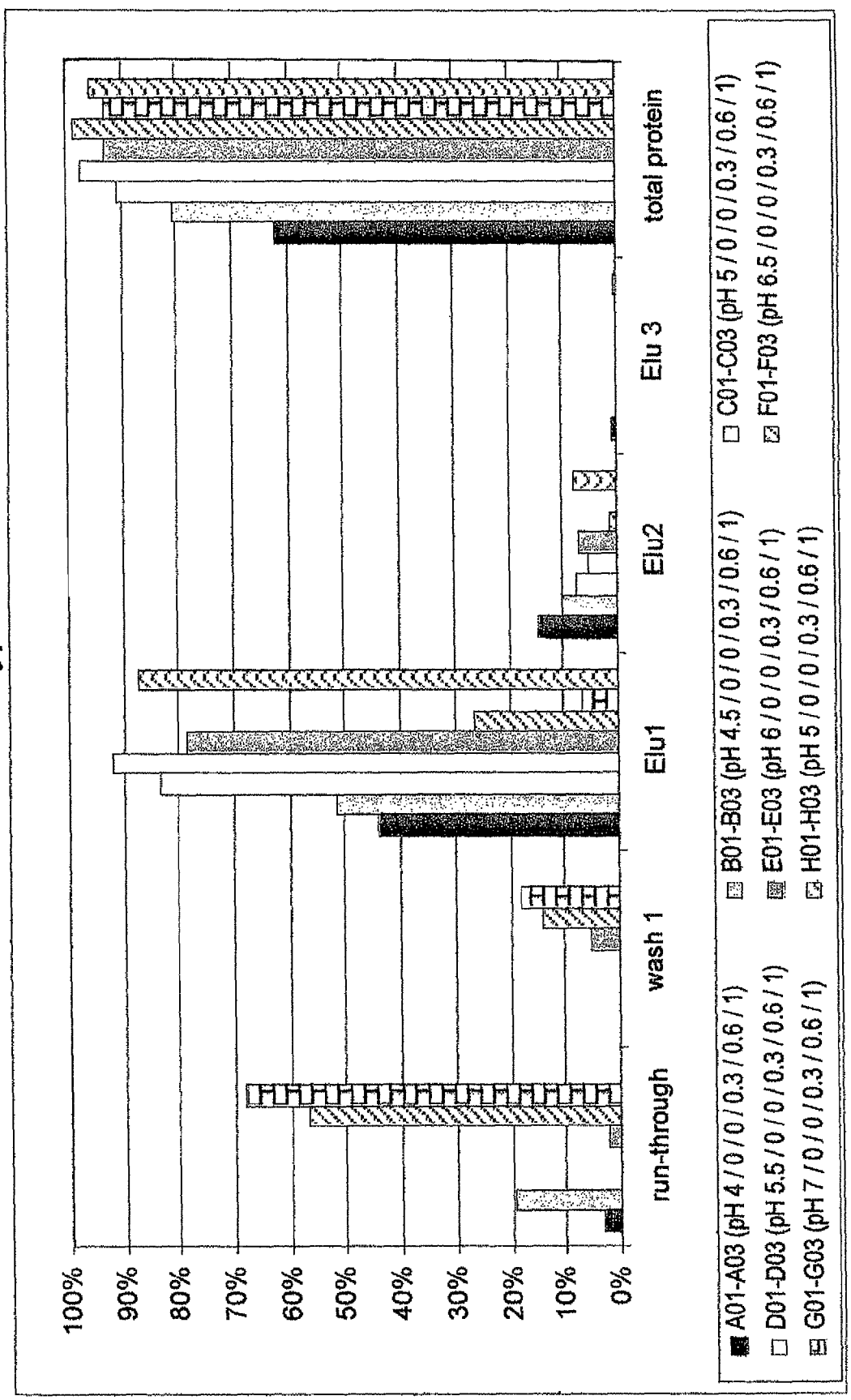
Fig. 3.5

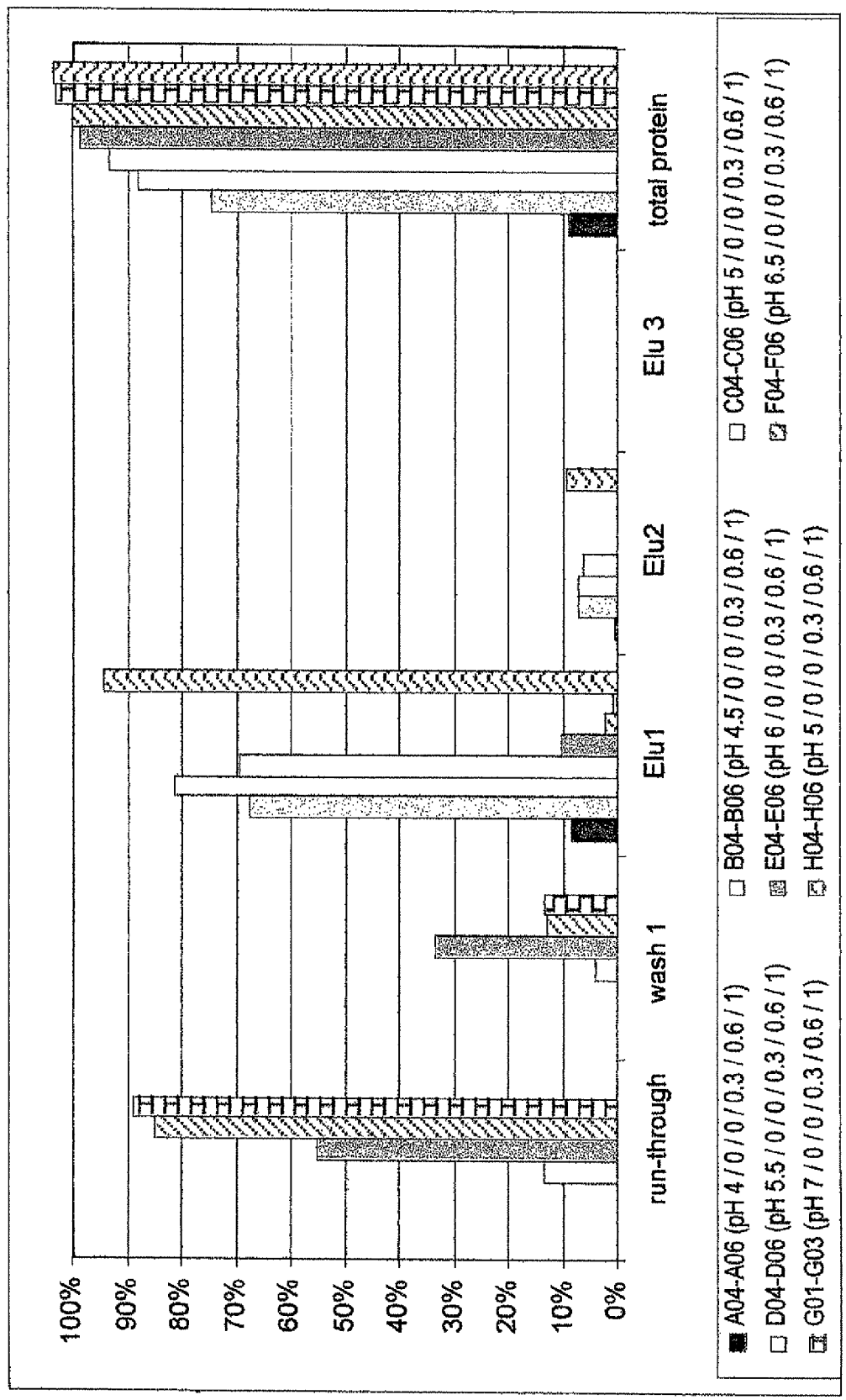
Fig. 3.6

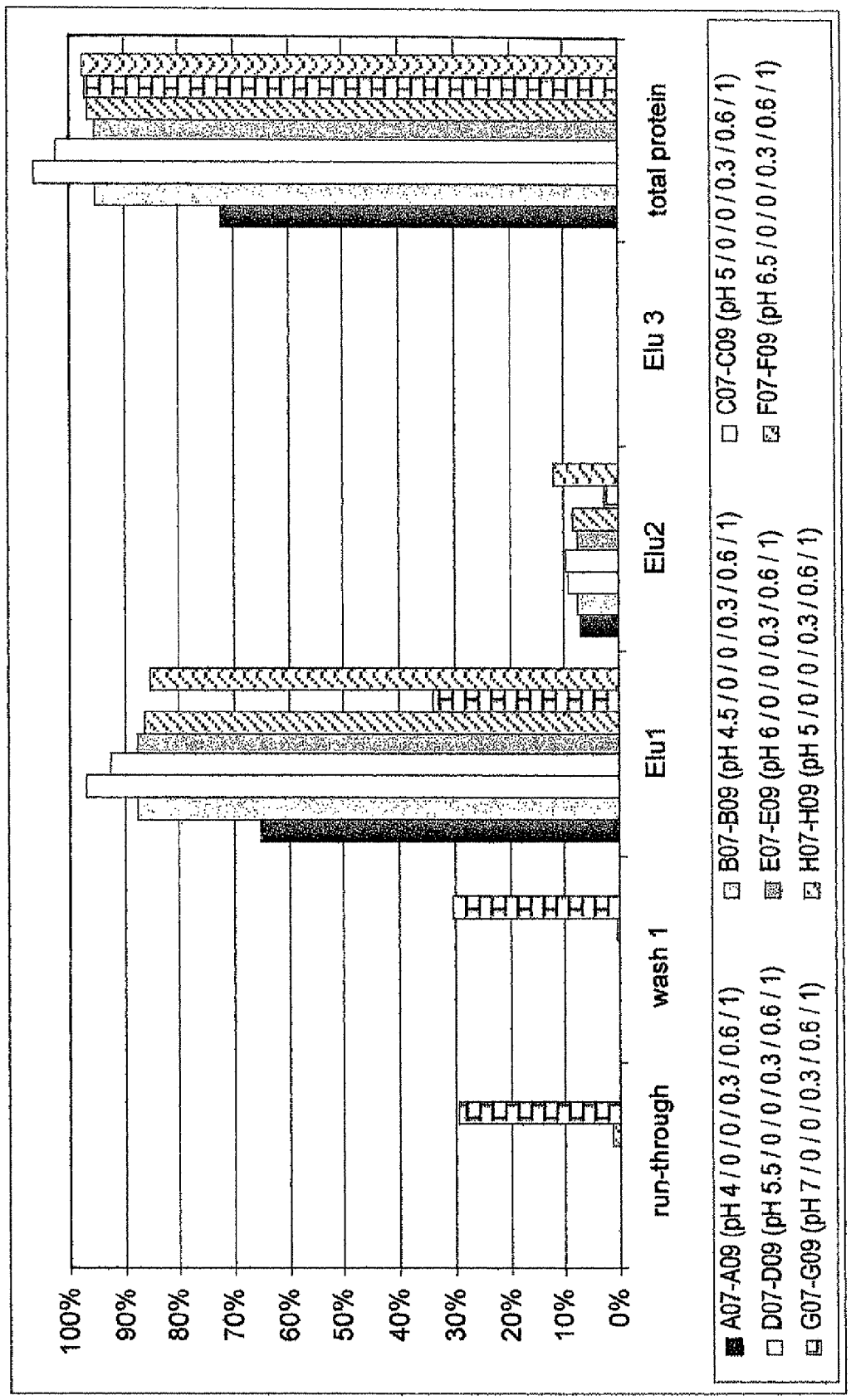
Fig. 3.7

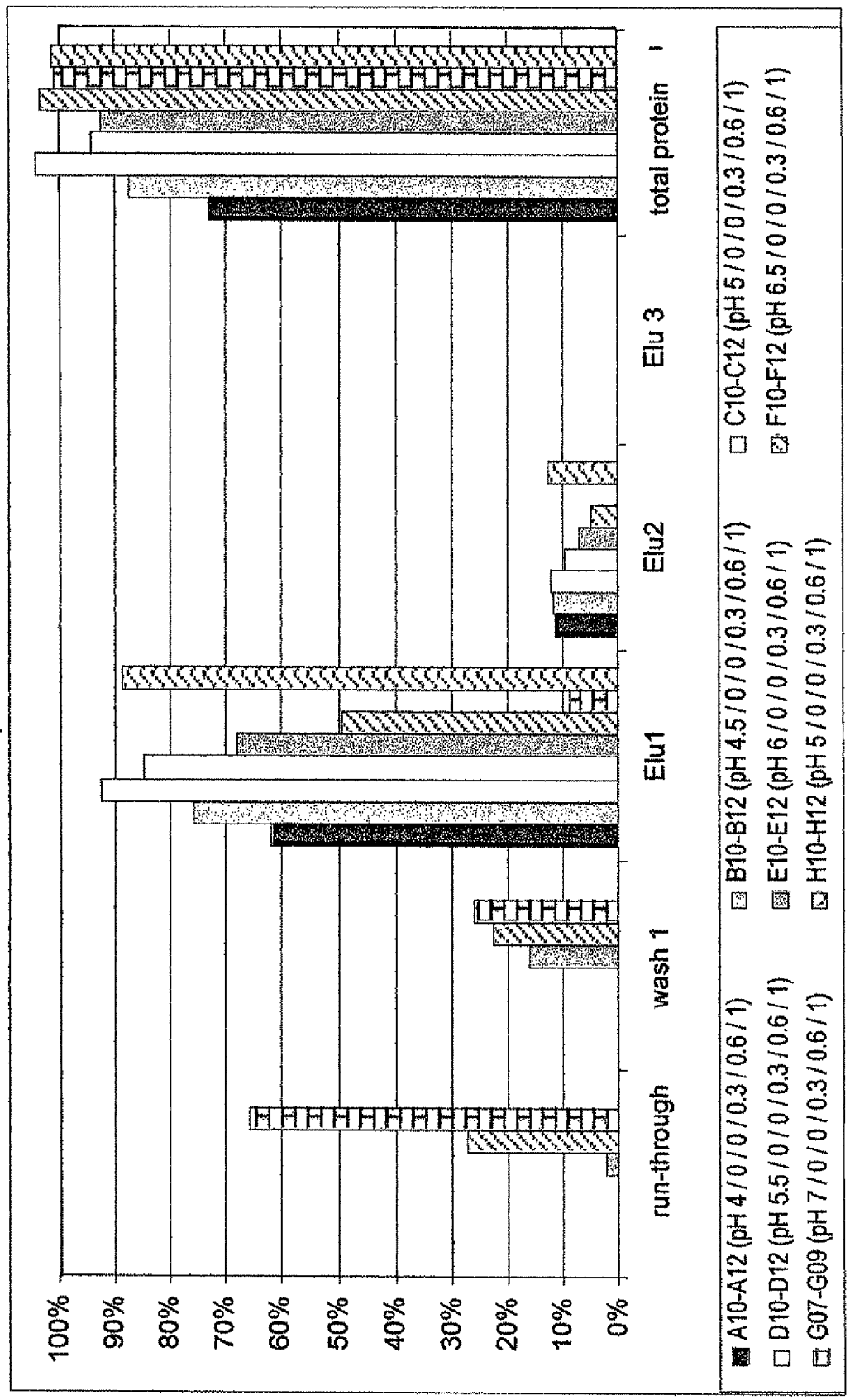
Fig. 3.8

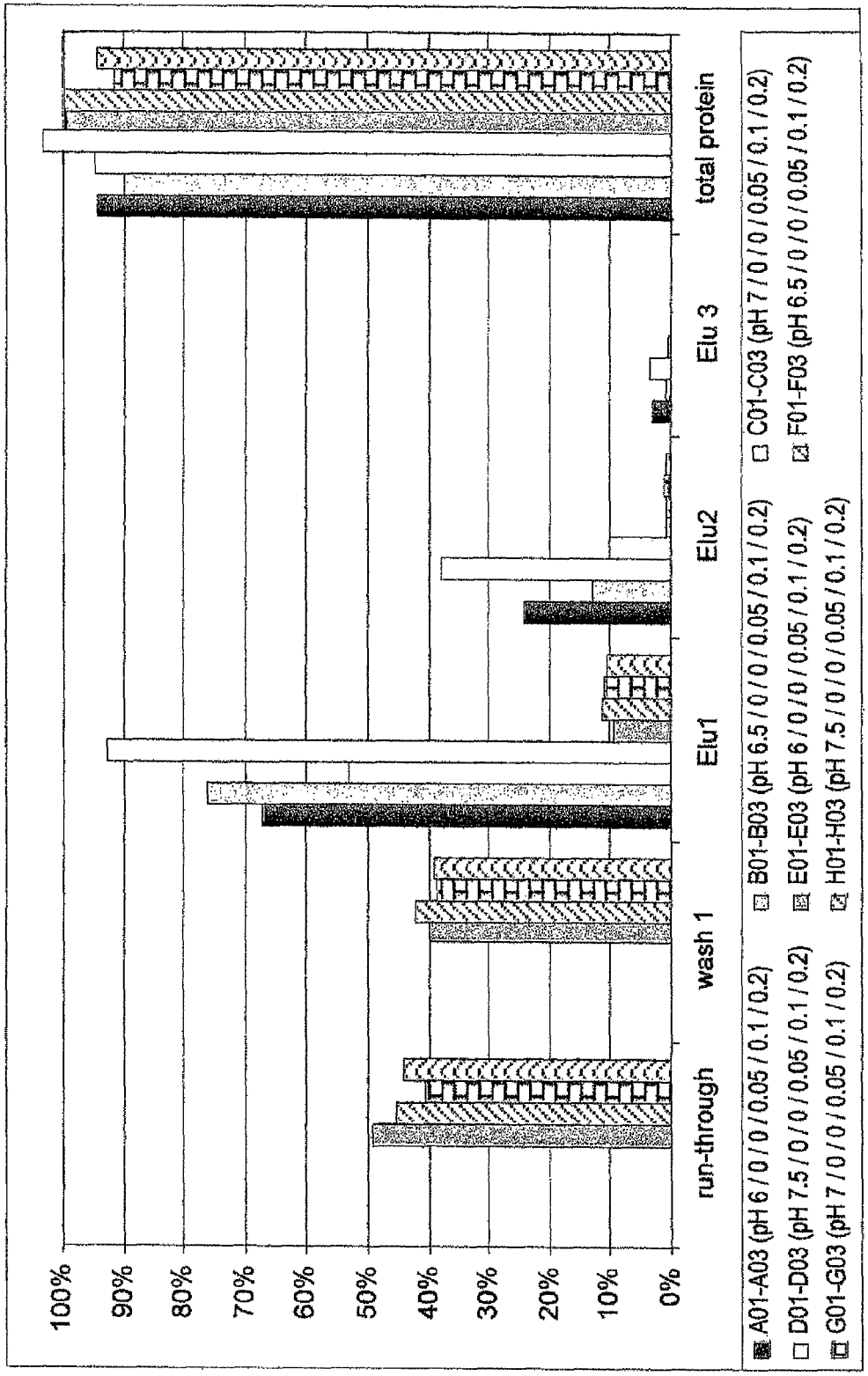
Fig. 3.9

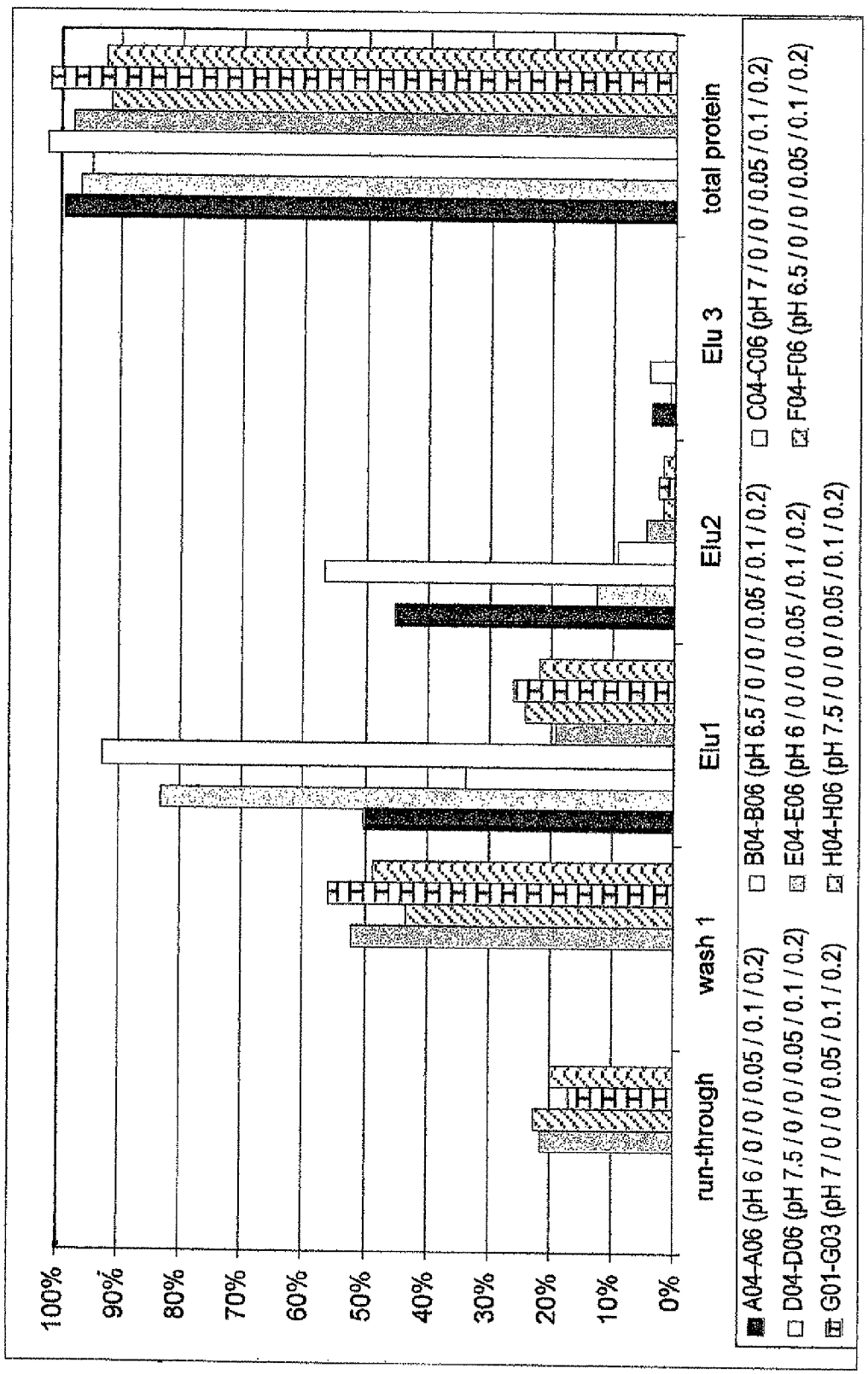
Fig. 3.10

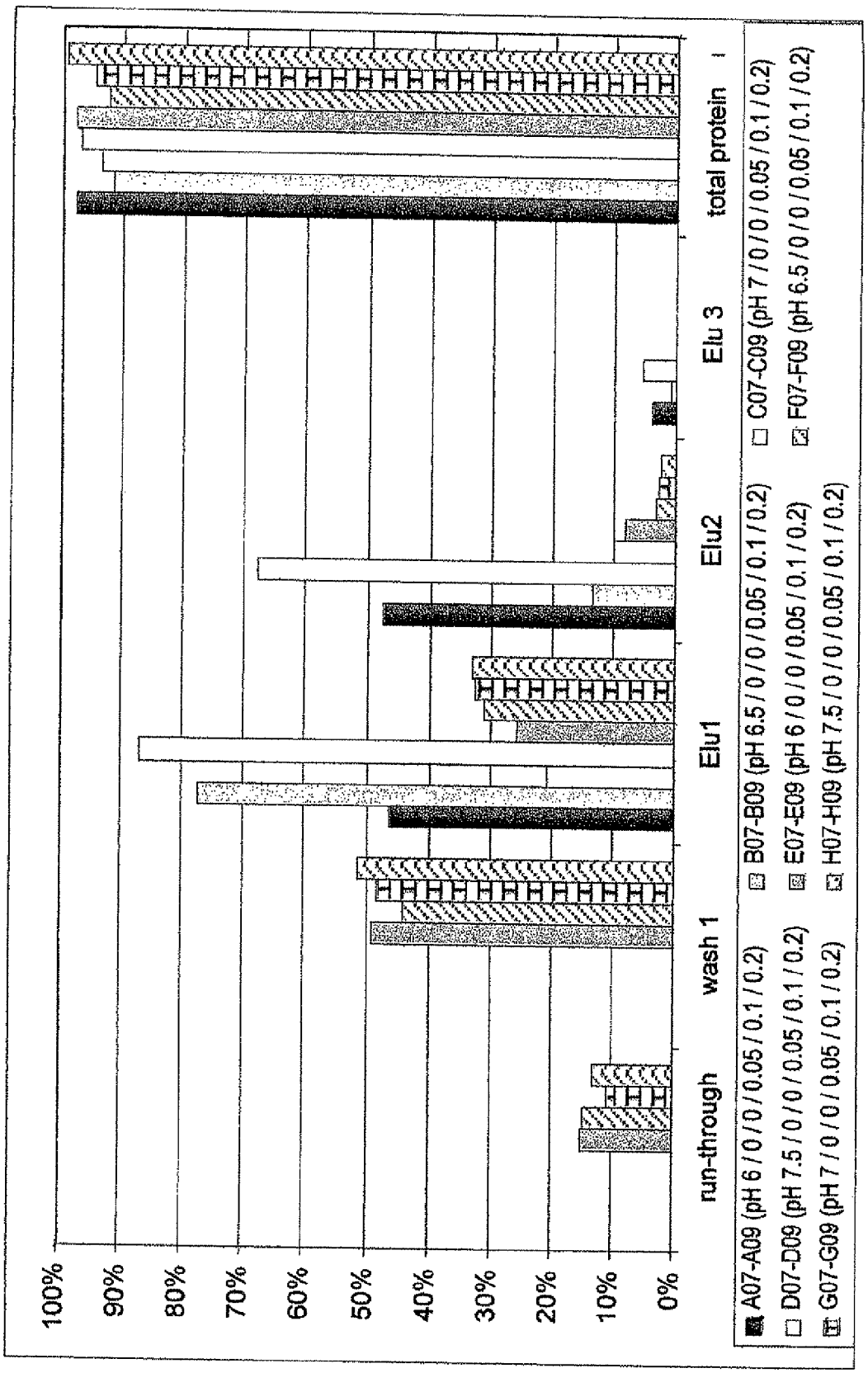
Fig. 3.II

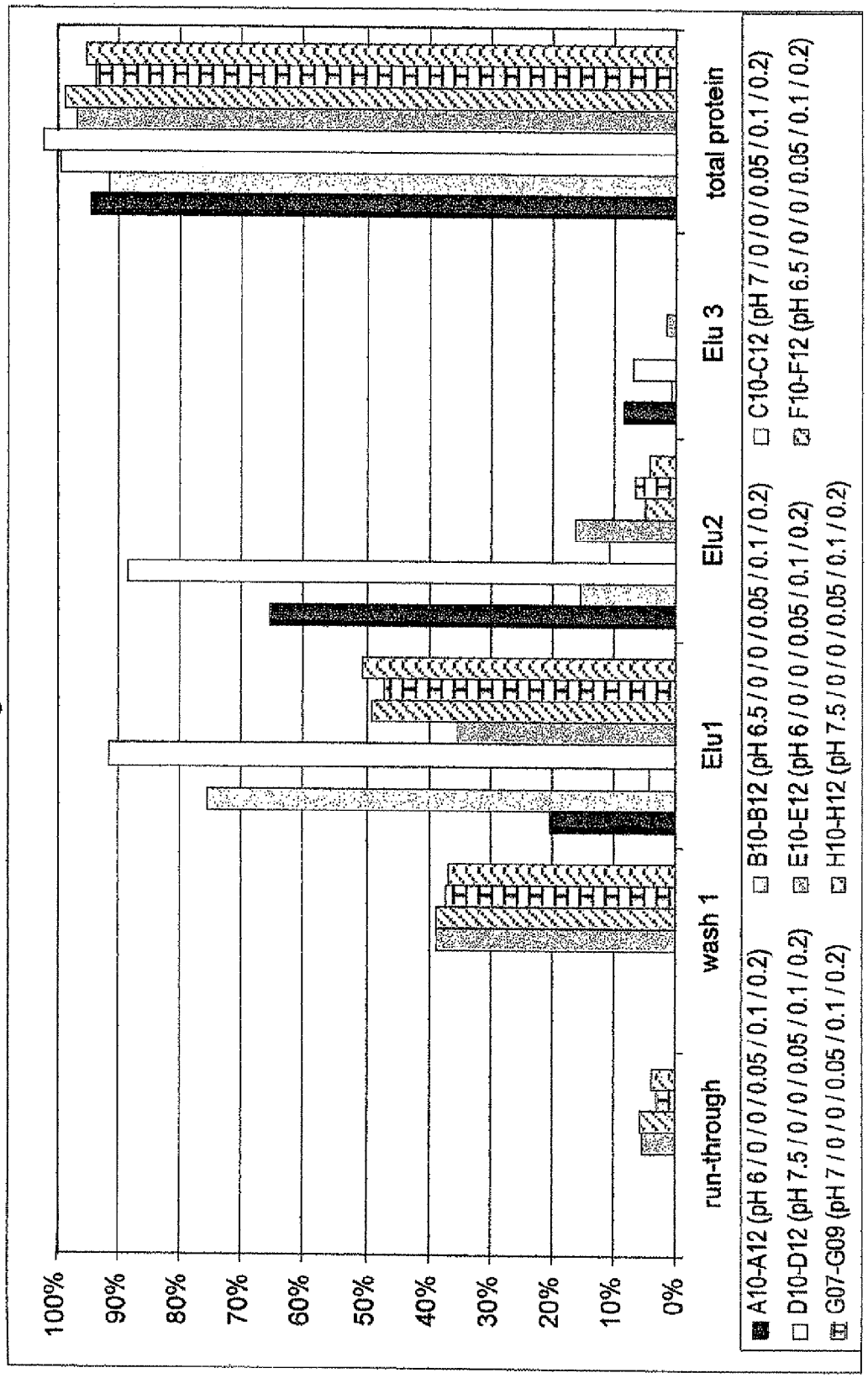
Fig. 3.12

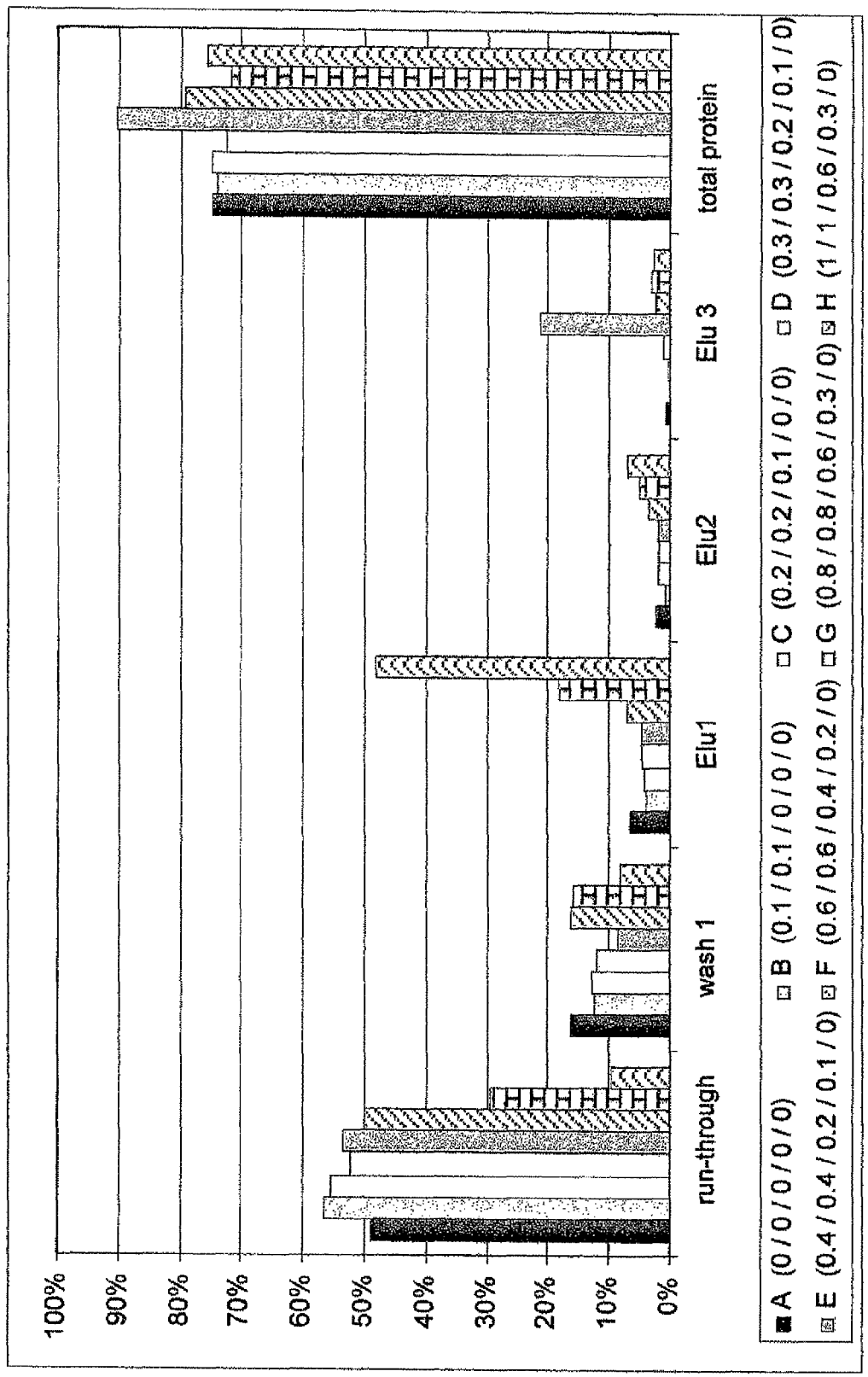
Fig. 5.1

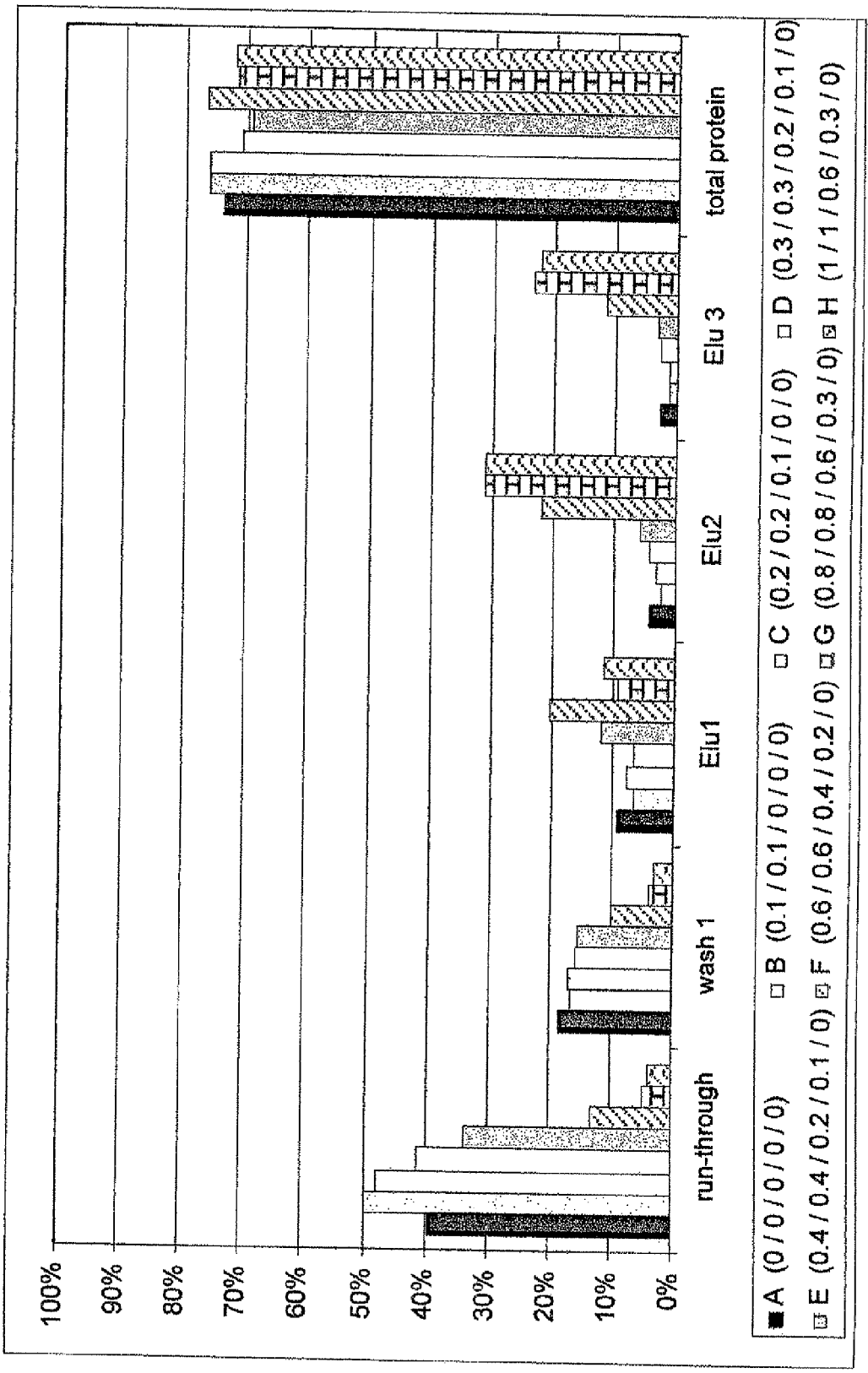
Fig. 5.2

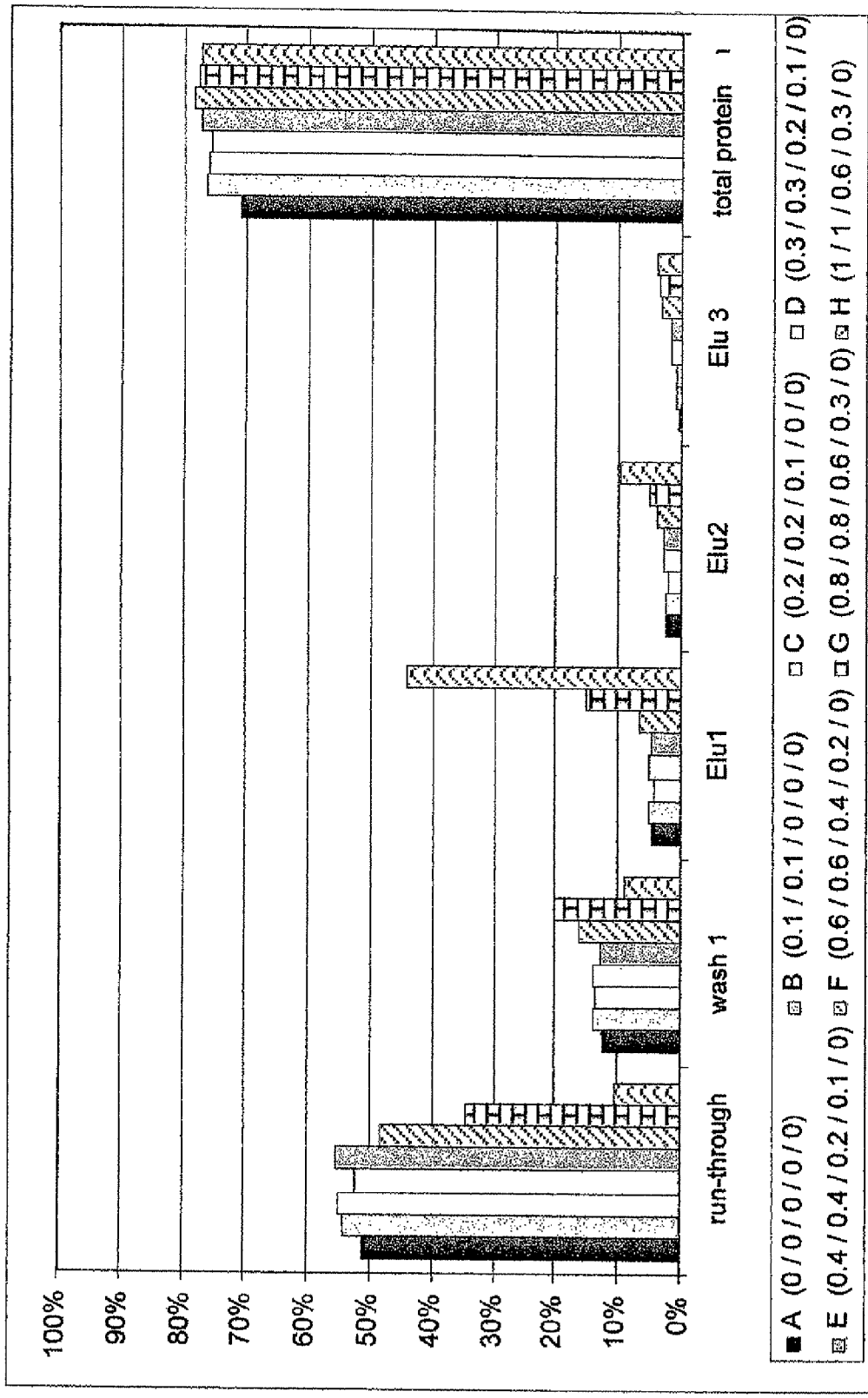
Fig. 5.3

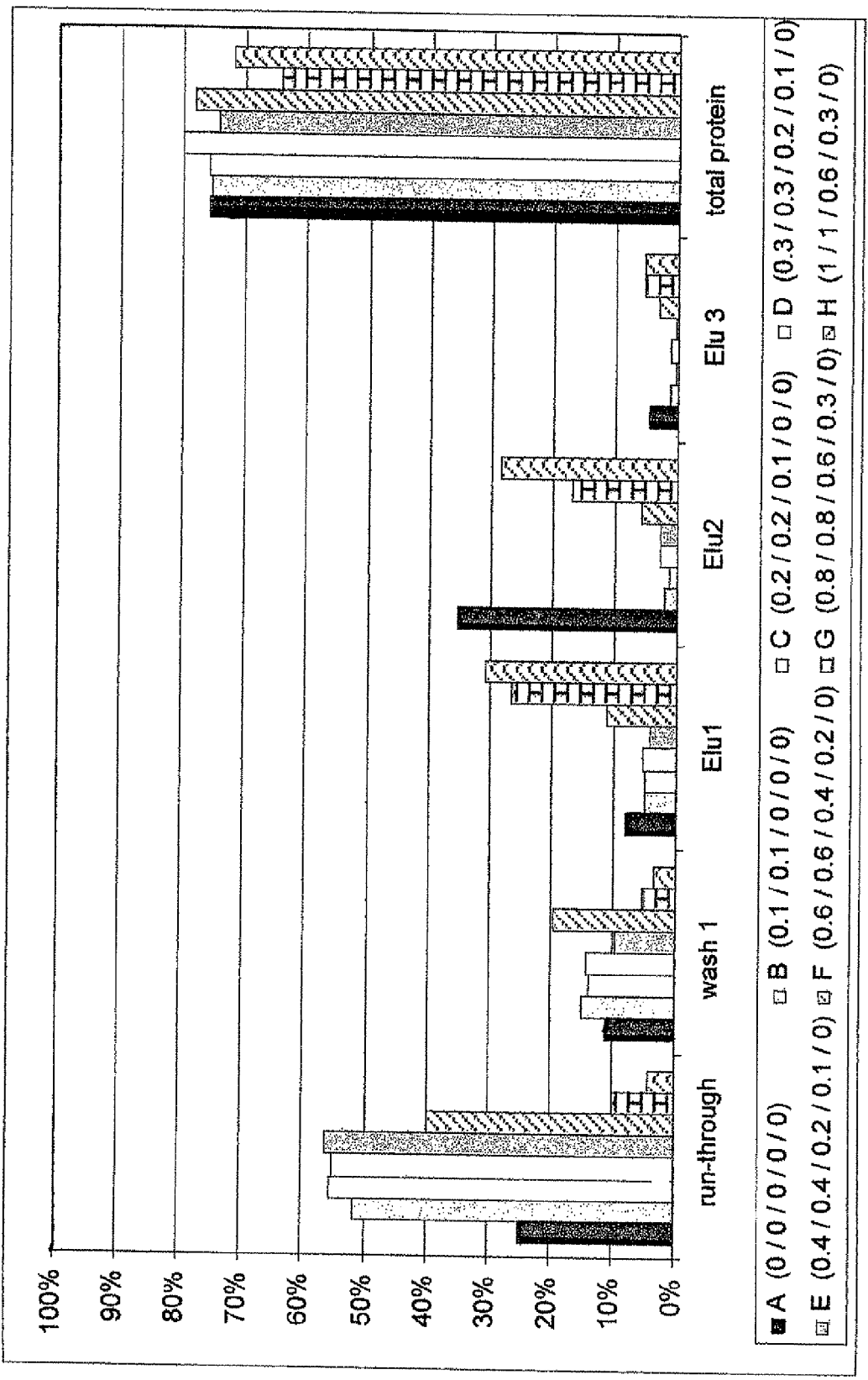
Fig. 5.4

METHOD FOR THE OPTIMIZATION OF CHROMATOGRAPHIC PURIFICATION PROCESSES FOR BIOLOGICAL MOLECULES

This application claims priority benefit from German application DE 10 2006 027 496.2, filed Jun. 14, 2006, and from U.S. provisional application Ser. No. 60/805,100, filed Jun. 19, 2006, the contents of which are incorporated herein in their entireties.

FIELD OF THE INVENTION

The invention relates to a method which allows the development and optimisation of chromatographic purification processes for biomolecules which can be carried out on a large scale.

BACKGROUND TO THE INVENTION

Biomolecules such as proteins, polynucleotides, polysaccharides and the like have increasingly been gaining commercial significance as medicaments, as diagnostic agents, as additives for foodstuffs, detergents and the like, as research reagents and for many other applications. The need for such biomolecules cannot generally be satisfied by isolating the molecules from natural sources—e.g. in the case of proteins—but require the use of biotechnological production methods.

The biotechnological production of proteins typically begins with isolating the DNA which codes for the desired protein and cloning it into a suitable expression vector. After transfection of the expression vector into suitable prokaryotic or eukaryotic expression cells and subsequent selection of transfected cells the latter are cultivated in fermenters and the desired protein is expressed. Then the cells or the cultured supernatant are harvested and the protein contained therein is worked up and purified.

In the case of eukaryotic expression systems, i.e. when using mammalian cell cultures such as CHO or NSO cells, in the last 15 years a one hundred-fold increase has been achieved in the concentration of the desired protein which can be achieved in the cell cultures or cell culture supernatants in the expression step. Over the same period the binding capacity of chromatography materials which are used during the subsequent purification of the proteins has only improved by a factor of 3. For this reason there is an urgent need for improved, optimised purification processes for biomolecules, particularly proteins, which can be carried out on a large industrial scale.

In the case of biopharmaceuticals, such as proteins used as medicaments, e.g. therapeutic antibodies, in addition to the product yield the removal of impurities is also of outstanding importance. A distinction can be drawn between process-dependent impurities and product-dependent impurities. The process-dependent impurities contain components of the host cells such as proteins and nucleic acids and come from the cell culture (such as media ingredients) or from the working up (such as salts or detached chromatography ligands). Product-dependent impurities are molecular variants of the product with differing properties. These include shortened forms such as precursors and hydrolytic breakdown products, but also modified forms produced for example by deamination, incorrect glycosylations or wrongly linked disulphide bridges. The product-dependent variants also include polymers and aggregates. The term contaminants is used to denote all other materials of a chemical, biochemical or microbiological nature which do not directly belong to the manufacturing process. Examples of contaminants include viruses which may undesirably occur in cell cultures.

Impurities and contaminants lead to safety concerns in the case of biopharmaceuticals. These are intensified if, as is very often the case in biopharmaceuticals, the therapeutic proteins are administered by injection or infusion directly into the bloodstream. Thus, host cell components may lead to allergic reactions or immunopathological effects. In addition, impurities may also lead to undesirable immunogenicity of the protein administered, i.e. they may trigger an undesirable immune response by the patient to the therapeutic agent, possibly to the point of life-threatening anaphylactic shock. Therefore, there is a need for suitable purification processes by means of which all undesirable substances can be depleted to an insignificant level.

On the other hand, economic aspects cannot be ignored in the case of biopharmaceuticals. Thus, the production and purification methods used must not jeopardise the economic viability of the biopharmaceutical product thus produced. In addition, the timescale within which a new purification process can be established plays an important role: Besides its influence on the costs, the process development must be in tune with the preclinical and clinical development of the drug. Thus, for example, some of the preclinical and all the clinical trials can only begin when sufficient quantities of the biopharmaceutical of sufficient purity are available.

The following standard process consisting of four basic steps may serve as a starting point for developing a purification process for an antibody which can be carried out on a large scale: In the first step the target protein is isolated, concentrated and stabilised ("capturing"). In the second step, viruses are eliminated, in the third step purification is carried out in which the majority of the impurities such as nucleic acids, other proteins and endotoxins are depleted. In the final step any remaining traces of impurities and contaminants are eliminated ("polishing").

In addition to filtration and precipitation steps, (column) chromatographic methods are of central importance. Thus, the capturing frequently includes a step of purification by affinity chromatography. Accordingly, there are numerous known column chromatographic methods and chromatography materials which can be used with them. With an increasing number of alternatives, ever greater numbers of preliminary trials have to be carried out, however, in order to determine the optimum materials and methods in terms of the purification effects, yield, biological activity, time, costs, etc.

When establishing and optimising a purification process it must also be borne in mind that it has to be tailored very individually to the biochemical and biophysical properties of the particular molecule to be purified (target molecule, target protein) and to the conditions under which the biological starting material was obtained. The biological starting material from which the target material has to be isolated generally consists of a very complex mixture of substances. In order to isolate and concentrate the target molecule, its specific properties such as shape, size, solubility, surface charge, surface hydrophobicity and biospecific affinity for binding partners are exploited. For each new target molecule, and even for the same target molecule with a variation in one of the preceding steps (e.g. a change in the composition of the cultivation medium for fermentation), the process has to be newly adjusted as it is possible that the best possible results from the above point of view will no longer be achieved under the new conditions.

At the same time, the number of theoretically conceivable alternatives in the process is potentiated by the number of parameters listed above. In column chromatography, for example, the arrangement of the chromatography step in the process as a whole, the column material, the pH, the salt content and the nature of the various eluant buffers used, the protein concentration when charging the column and many other aspects have to be optimised. This makes it virtually impossible to develop an optimised column chromatography process on an industrial scale at reasonable cost and in a reasonable time frame. On the other hand the economic viability and also equipment related restrictions (such as the need to use as few different buffers as possible and the smallest possible amounts or volumes of buffer and chromatography materials, to keep the volumes of product-containing fractions as small as possible and the need to minimise the processing times and also the volumes of waste water) demand such optimisation for each individual step of the process.

Conventionally, this problem is approached by successively varying a limited number of process parameters in more or less systematically conducted preliminary trials on the "trial and error" principle and ending these trials as soon as a basically "functioning" process can be found. Thus there is virtually no or only very limited systematic optimisation of all the essential parameters of a process, possibly from a number of points of view, e.g. with respect to the depletion of impurities, high product yields with simultaneously small losses of biological activity and the like. Processes established in such a way are consequently generally less than ideal.

Alternatively, attempts have been made to carry out the above optimisations using small columns on a laboratory scale (e.g. small columns containing about 1 ml of chromatography material). However, it was found that only a limited number of parameters could be varied at reasonable cost as the charging, washing and elution steps took a great deal of time, even on this smaller scale.

Another approach to optimising processes on a miniaturised scale can be found in WO2004/028658. The binding of a biological sample to chromatography materials is tested in parallel batches on multi-well plates in a batch method. Admittedly this process allows optimum conditions for this binding step to be determined quickly and cost-effectively. However, it is not possible to tell whether, under the conditions thus specified, optimum results can still be achieved in the column chromatography methods which are necessarily used under industrial-scale conditions. Also, this optimisation of the process relates only to optimising the step of charging the chromatography material, i.e. only a small part of the process as a whole.

Therefore, there is still an urgent need for processes by which column chromatographic methods of purification of biomolecules can be established and optimised quickly and cheaply, while these processes must also deliver satisfactory results under the conditions of large scale industrial production and purification of the biomolecule. The aim of the invention is to provide such a process.

SUMMARY OF THE INVENTION

The problem stated above is solved by the methods recited in the claims.

In particular, the invention provides a method of finding suitable parameters for chromatographic processes for separating or purifying biological molecules, in which a sequence of equilibration, charging, washing and elution steps is completed in a partial batch method (steps with and without suspension of the chromatography material), on a small scale, e.g. with a gel bed volume of chromatography material of between 0.01 and 2 ml. In this way, one or more parameters can be varied in a number of tests and from the results of these tests conclusions can be drawn as to the optimum conditions under which the chromatographic process can be carried out. The optimised conditions thus determined can then be applied to chromatographic methods, particularly column chromatographic methods, which are carried out on a larger scale.

By the phrase "partial batch method" is meant that in one or more of the specified steps—but not all the steps—the chromatography material is suspended, i.e. processed in a batch process. The steps in which no suspension of the chromatography material takes place are carried out in the manner of "conventional" column chromatography, by applying the particular buffer solution, e.g. an elution buffer, to a deposited gel bed, without causing suspension of the gel bed, and allowing the buffer to run through the column material, directed for example by gravity, centrifugation, the application of a pressure gradient or the like.

According to the invention it has proved particularly useful, for solving the above mentioned problem, to carry out the "partial batch method" such that during the charging step the chromatography material is suspended but during the elution step (or steps, in the event of several elution steps) suspension of the chromatography material is avoided and instead the eluant solution is moved in directed manner through the deposited gel bed.

If optimum charging, washing and/or elution conditions for the particular chromatography material and the biomolecule to be purified are to be determined on a small scale, e.g. using between about 50 μl and 2 ml of chromatography material, according to the partial batch method described above (by for example varying the parameters of the pH and/or ion intensity of the individual solutions, protein concentration and the like and determining optimum results with regard to the purification effect, yield and biological activity of the biomolecule), these conditions can surprisingly be transferred highly reproducibly to column chromatographic methods, even on a larger scale, even if the latter are carried out not by the partial batch method but in the conventional way as pure column chromatographic methods, i.e. in a manner that can be scaled up to industrial quantities. In other words, the partial batch method carried out on a miniature scale can be used as a "model" for column chromatographic methods. The miniaturisation allows substantially cheaper and faster operation compared with conventional optimisation processes. In addition, according to a preferred embodiment, the miniaturised test batches can be carried out in large numbers in parallel by the use of suitable sample containers (such as multi-well filter plates, for example) and equipment (multi-channel pipettes, pipetting robots) and a number of parameters can be varied simultaneously. The result is that a large amount of data are obtained from which it is possible to determine the column chromatography conditions for a particular biomolecule to be purified, optimised simultaneously in respect of all the critical parameters. An optimising process of this kind is thus inexpensive and quick to carry out and constitutes serious progress in terms of the optimum selection of suitable parameters for chromatographic separation methods. Thus, this method makes a major contribution to improving the processes for purifying biomolecules and hence also to the quality and economic viability of the products in which a biomolecule of this kind is used.

BRIEF DESCRIPTION OF THE FIGURES

FIG. 3 shows in graph form the results of experiments described in Example 3, the 8 figures FIG. 3.1 to FIG. 3.8 showing the results of a "binding screening" with 8 different chromatography materials while the 4 figures FIG. 3.9 to FIG. 3.12 show the results of an "elution screening" with 4 different chromatography materials. The percentage proportions of the total amount of protein used per cavity in the run-throughs or eluates in the charging step ("run-through"), the washing step ("Wash1"), the 3 elution steps "Elu1" to Elu3" and the total amount of protein recovered (total protein) are shown. Within each group of four bars shown in the diagram the individual bars indicate the results at different pH and salt concentrations indicated in the caption.

FIG. 5 graphically shows the results of the experiments described in Example 5, FIG. 5.1 to FIG. 5.4 showing the results of the screenings with 4 different chromatography materials. The percentage proportions of the total amount of protein used per cavity in the run-throughs or eluates in the charging step ("run-through"), the washing step ("Wash1"), the 3 elution steps "Elu1" to Elu3" and the total amount of protein recovered (total protein) are shown. Within each group of 8 bars the individual bars show the results at different salt concentrations indicated in the caption.

DETAILED DESCRIPTION OF THE INVENTION

Figure 1:
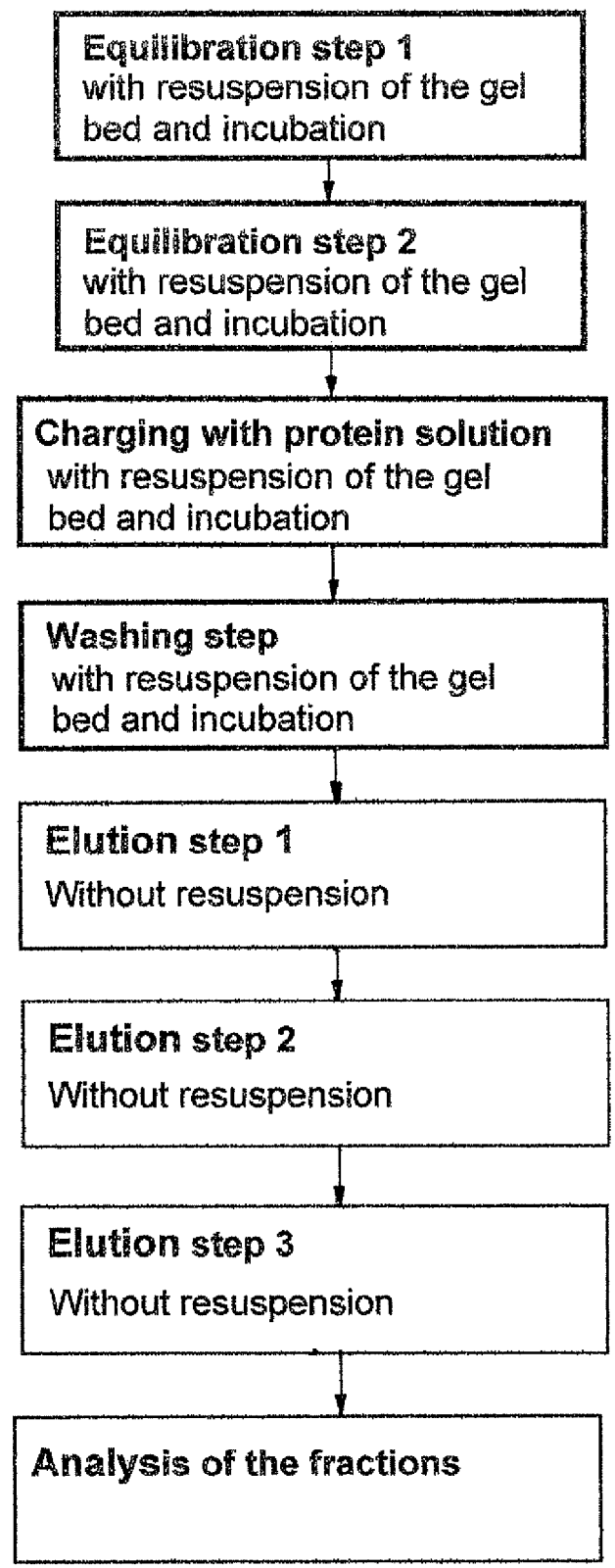
FIG. 1 shows a flow diagram, illustrating a partial batch method according to a particularly preferred embodiment of the invention.

According to the invention, a method of finding suitable parameters for chromatographic methods of separation (purification) of biological molecules is provided, the chromatographic method comprising (one or more) equilibration steps, (one or more) charging steps, (one or more) washing steps and (one or more) elution steps, characterised in that the sequence of equilibration, charging, washing and elution steps is carried out in a partial batch method. Preferably, the charging step at least comprises suspending the chromatography material and suspension of the chromatography material is omitted in at least one elution step. According to one embodiment of the invention the chromatography material is suspended during the equilibration step (or equilibration steps). According to two other alternative embodiments of the invention the chromatography material is suspended or not suspended in the washing step or washing steps. In all these embodiments, the partial batch method is used, which consists in carrying out part of the process—at least the charging step—with suspension of the chromatography material (i.e. by a batch process) while in another part—at least during elution of the biomolecule—in the manner of column chromatography, the chromatography material is not suspended, but instead the elution buffer is applied to the non-suspended gel bed and then the eluate is recovered by centrifugation, the application of a pressure gradient or the like.

By "chromatography materials" are meant all the materials conventionally used for column chromatography. These can be divided into materials for:

affinity chromatography,
ion exchange chromatography, particularly anion-ion exchange and cation exchange chromatography,
hydrophobic interaction chromatography,
"reversed phase" chromatography,
hydroxy-apatite chromatography,
"hydrophobic charge induction" chromatography and
"mixed mode" chromatography, although the invention is not restricted to these groups or to the materials expressly mentioned hereinafter.

Materials for affinity chromatography contain a ligand bound to a carrier material which causes selective and specific binding of the biomolecule to be purified to the chromatography material. Ligands frequently used for the purification of anti-bodies are protein A, a cell wall protein from *Staphylococcus aureus*, and numerous variants and derivatives thereof.

Examples of functional groups on chromatography materials suitable for anion exchange chromatography include the quaternary hydroxypropyldiethylaminoethyl group, the quaternary trimethylaminoethyl group or the diethylaminoethyl group. Suitable groups for cation exchange chromatography include, for example, the sulphomethyl group, the sulphopropyl group and the carboxymethyl group.

In hydrophobic interaction chromatography, for example, alkyl and aryl ligands may be used, such as ether and methyl ligands (weaker interaction with proteins), or butyl, phenyl and octyl ligands (strong interaction).

In reversed phase chromatography, alkyl or aryl ligands are also used, although the ligand density is typically higher than in hydrophobic interaction chromatography.

For "mixed mode" and "hydrophobic charge induction" chromatography, in particular, ligands are used which depending on their pH enter into different interactions with the biomolecule (such as MBI HyperCel® Sorbent and MEP HyperCel® Sorbent by BioSepra).

The equilibrating buffer solutions, test solutions, washing solutions and elution solutions (hereinafter generally referred to as "buffer solutions") may be solutions based on e.g. phosphate, Tris, acetate, citrate or glycine buffer.

The suspension of the chromatography material is carried out for example by (high frequency) shaking of the sample vessels (e.g. using a mechanical shaker) or by pipetting the chromatography material on and off.

In the charging step, in particular, it may be necessary to carry out an incubation step after the addition of the test solution containing the biomolecule to the chromatography material. If the chromatography material is incubated with the test solution for too short a time the problem may arise that the biomolecule has not fully bound to the chromatography material before the test solution is replaced by the washing solution. If the incubation time is too long, there is a danger with many biomolecules that denaturing of the biomolecule will set in. Depending on the type of biomolecule, the test buffer and the chromatography material, therefore, the incubation period must be selected between the extremes stated above. Frequently, the optimum incubation period determined will not exceed 120 min. Preferably incubation is no longer than 60 min. Incubation periods of less than 30 min are particularly preferred.

The "washing step" according to this invention is the step that follows the charging of the chromatography material with the biomolecule. Depending on the particular problem encountered, the intention may be to elute the biomolecule during this step. In this case the washing step constitutes an elution step, i.e. the washing and elution steps coincide.

Depending on the particular problem the test solution during the charging step may contain a defined biomolecule or a mixture of biomolecules. Depending on the particular question the defined biomolecule may be, for example, a protein which is to be purified on a large scale in the process which is to be established and optimised, or a defined impurity such as, for example, aggregates of the protein which is to be purified, or protein A (in order to investigate the removability of "leach protein A" optionally released from a protein A column in a preceding purification step). The mixture may be, for example, a cell lysate, optionally after previous centrifugation and/or filtration steps, such as for example a mixture of host cell proteins (HCP) with over-expressed target protein, which is to be used as starting material for the purification on a large scale at a later stage.

As explained previously, the batch method described above and carried out on a small scale may be used to determine the chromatography conditions under which the corresponding column chromatographic purification process which is to be carried out on a large scale will yield optimum results. Whether the conditions selected, such as the nature of the chromatography material, the type of buffer, ion intensity/conductivity, pH, etc, will give better or worse results, can be determined in the usual way by analysing the run-throughs of at least the elution step or steps for their quantity and quality (e.g. biological activity still present) of the eluted biomolecule. Preferably, moreover, the run-through from the charging step and the washing step (or washing steps) is collected and analysed in the same way in order to obtain a full picture of the binding properties of the biomolecule in these steps under the conditions selected. The nature of working up and analysing the run-throughs and eluates depends on the nature of the chromatography and the sample material, i.e. the biomolecule or mixture of biomolecules. In the case of protein A affinity chromatography and the charging of the column with a mixture of HCPs and over-expressed target protein (immunoglobulin) it will be interesting, for example, to discover how great a proportion of the immunoglobulin added during the charging step with the test solution has bound to the chromatography material (i.e. cannot be found in the run-through from the charging step), the quantity of immunoglobulin and impurities which appears in the run-through from the washing step or steps, and the quantity and purity in which the immunoglobulin can be found in the eluate from the elution step or steps and what proportion still has the desired biological activity. These findings can be obtained in the conventional manner, e.g. using spectroscopic methods and other methods of measuring proteins. The quantity of impurities can be disclosed and quantified, for example, using SDS-gel electrophoresis or isoelectric focusing methods.

According to one particular embodiment of the invention, in ion exchange chromatography, charging and elution conditions are optimised in separate experiments (binding and elution screening) and several elution steps are provided during the elution screening in any event, the salt concentration, for example, being changed stepwise in each step.

In a preferred embodiment the equilibration, charging, washing and elution steps are carried out in a number of parallel test batches. In order to determine the optimum chromatography conditions, these conditions are expediently varied in the individual test batches, so that from the purification results which can be achieved in the parallel experiments conclusions can be drawn as to the optimum chromatography conditions for the particular biomolecule and/or chromatography material. The running of parallel experiments can be achieved using a multi-well filter plate on which a plurality of sample containers are provided into which the chromatography material and the buffer solutions (such as equilibrating buffer solutions, test solutions optionally containing a biomolecule, washing solutions and elution solutions) are placed, these containers being closed off at the bottom by a material with filtering properties which allows the buffer solution but not the chromatography material to escape. Multi-well or microtitre filter plates of this kind are obtainable for example under the brand name Captiva® by Varian® (96 wells, pore size 0.45 μm), MultiScreen® by Millipore® (96 wells, pore size 0.22 μm, 0.45 μm and 0.65 μm) and Silent Screen® by Nunc® (96 wells and a pore size of 0.45 μm). The chromatography solutions and buffer solutions can be pipetted into the sample containers on the plate using a conventional multi-channel pipette or pipetting robot (e.g. Freedom Evo 150® made by Tecan®).

The volumes of the chromatography materials and buffer solutions pipetted into the wells may vary and are preferably in the range from 0.01 to 2 ml, more preferably in the range from 0.05 to 2 ml when using one of the above mentioned filter plates with 96 wells. During the initial charging of the filter plates with chromatography material it has proved advantageous first to rinse the filter plate with e.g. a 20% or 10% ethanol solution and then add the chromatography material as a 1 to 60% (w/v) suspension in 20% or 10% ethanol solution.

Carrying out the process according to the invention in parallel test batches allows a number of column chromatography parameters to be optimised simultaneously and thus opens up the possibility of developing, in a very short time and with smaller amounts of material, a column chromatography process which will also yield excellent purification results even on an industrial scale under the conditions thus determined. In this way better processes can be achieved and costly development time and espensive materials (chromatography material, biomolecules, etc) can be saved.

According to a most particularly preferred embodiment the process is carried out according to the following sequence of steps (see also FIG. 1):

(a) a suspension of a chromatography material is placed in a plurality of wells (sample containers) in a multi-well filter plate, (b) a moist gel bed is produced in the wells containing the suspension, by removing the supernatant above the chromatography material by centrifugation or by the application of a pressure differential, (c) in order to equilibrate the chromatography material contained in the wells an equilibrating buffer solution is added to the moist gel bed and the gel bed is suspended and optionally incubated with the solution for a certain length of time (equilibration step), (d) a moist gel bed is produced according to step (b), (e) optionally steps (c) and (d) are repeated several times, in particular once, twice or three times, (f) in order to charge the chromatography material a test solution is added to the gel bed, containing at least one biomolecule, and the gel bed is suspended and optionally incubated with the charging solution (charging step), (g) a moist gel bed is produced according to step (b), (h) in order to wash the chromatography material a washing solution is added to the gel bed, the gel bed optionally being suspended and optionally incubated again (washing step), (i) a moist gel bed is produced according to step (b), (k) optionally steps (h) and (i) are repeated several times, particularly once, twice or three times, while the washing solutions used may contain the same or different compositions and optionally the gel bed is suspended or is not suspended, (l) for eluting the biomolecule, an eluting solution is added to the gel bed without causing suspension of the gel bed (elution step), (m) according to step (b) a moist gel bed is produced and the eluate is collected, (n) optionally steps (l) and (m) are repeated several times, particularly once, twice or three times, while the eluant solutions used may have the same or different compositions, and (o) the eluates collected are analysed.

After analysis of the eluates and the other run-throughs which may have been collected, for their concentration and biological activity (such as specific binding properties) using conventional methods, the skilled man will be in a position to tell which test batch has produced the best results and can thus conclude under which conditions the individual steps have to carried out in order to obtain optimum results.

The invention is hereinafter described more fully with reference to examples, without restricting the subject of the invention to these examples.

EXAMPLES

Example 1

General Instructions for Carrying Out The Process According to One Embodiment of the Invention (Automated Method in a Number of Parallel Test Batches)

A multi-well filter plate is rinsed in a first step with 20% ethanol solution. To do this, the solution is poured into the plate and this is centrifuged, the ethanol solution thus centrifuged off being caught in a microtitre plate placed underneath and then discarded. The filter plate is then filled with the respective suspensions of the chromatography materials. If necessary, more 20% ethanol solution can be added to the suspensions. Centrifugation causes the material to be deposited and the liquid is eliminated to a point where the materials are not quite dry. The run-through is also discarded. Then equilibration of the chromatography material takes place (cf. also FIG. 1). For this purpose, buffer corresponding to the equilibration conditions is added to the chromatography material. Then the plate is incubated at maximum speed on the microtitre plate shaker in order to mix the buffer and material and then the buffer is centrifuged off again and discarded. This step is repeated once according to the overview shown diagrammatically in FIG. 1 by way of example.

In the subsequent charging step the prepared protein solutions, which have previously been adjusted to have the same pH levels and salt contents as in the equilibration, are added to the chromatography material and incubated on the microtitre plate shaker. The filtrate forms the run-through (FT). In the subsequent washing and elution steps, correspondingly adjusted buffers (see for example Examples 3 and 5) are added to the chromatography materials. Optionally further shaking and incubation can also be carried out during the washing steps, while during the elution there is no such shaking ("partial batch method"). The liquid phase is centrifuged off in each case. The filtrates from the washing steps are indicated by "W" or "Wash" and a progressive number, while those from the elution steps are analogously marked "E" or "Elu" and a progressive number. At the end, 150 µl of all the undiscarded filtrates are transferred into suitable microtitre plates for photometric measurement of their content at 280 nm.

Preferably, during equilibration, charging and washing, the mixtures are shaken and incubated. During elution, which is typically carried out (see e.g. Examples 3 and 5) with variation of the pH and/or salt content, the elution buffer by contrast is carefully added to the chromatography materials and immediately centrifuged fully without mixing and incubation.

Table 1 shows a typical sequence of the above steps, including data provided by way of example on typical incubation periods. The washing buffer corresponds to the equilibration buffer in its pH and salt content. The volumes and centrifugation settings are adjusted in this case to the Silent Screen® Multi-Well filter plate made by Nunc®. 2200 rpm (revolutions per minute) correspond to a relative centrifugal acceleration of 1012 g, 1200 rpm correspond to 301 g. Incubation is carried out on the microtitre plate shaker at maximum speed, i.e. about 1400 rpm:

TABLE 1

| Step | Addition of Liquid | | Incubation | Centrifugation | | |
|---|---|---|---|---|---|---|
| | Volume | Type | Period | Speed | Duration | Frequency |
| Rinsing | 350 µL | 20% ethanol solution | — | 2200 rpm | 1 minute | 1× |
| Filling with Chromatography media | 100 µL<br>100 µL | Suspension<br>20% ethanol solution | — | 1200 rpm | 1 minute | 1× |
| Equilibration | 200 µL | Equilibration buffer | 5 minutes | 1200 rpm | 1 minute | 2× |
| Charging | 200 µL | Protein solution | 21 minutes | 1200 rpm | 1 minute | 1× |
| Washing | 200 µL | Washing buffer | 9 minutes | 1200 rpm | 1 minute | 0-4× |
| Eluting | 200 µL | Eluting buffer | — | 1200 rpm | 1 minute | 0-5× |

Figure 2:
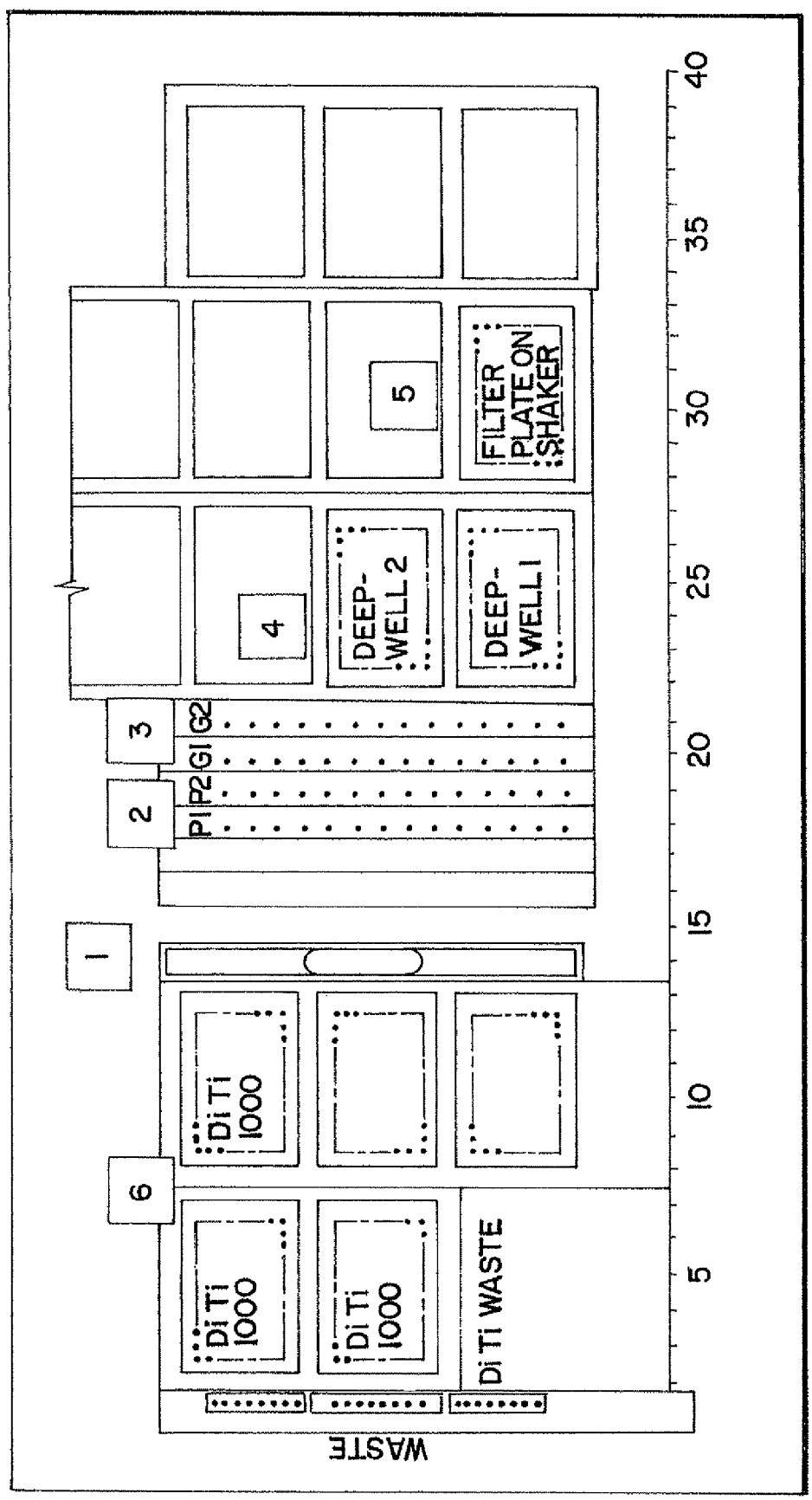
FIG. 2 schematically shows a test arrangement using a robot. It shows: A trough containing ethanol solution (1), sample vessels containing protein solutions (2), sample vessels containing suspensions of the chromatography materials (3), microtitre plates with equilibration, washing and eluting buffers (4), microtitre filter plate (5) and a supply of pipette tips (6).

For automatically carrying out a number of parallel tests a pipetting robot is preferably used. FIG. 2 shows a typical arrangement which can be used in this type of method. The trough (1) contains the above mentioned ethanol solution. The test vessels (2) and (3) hold the test solutions containing the biomolecule and adjusted to suitable pH values and salt concentrations and the suspensions of the chromatography materials. At position (4), microtitre plates/DWPs are provided which contain the equilibration, washing and elution buffers. Next to them is provided the multi-well filter plate (5).

Example 2

Comparison of Two Embodiments of the "Partial Batch Method" with a (Total) Batch Method The partial batch method was compared with a batch method. In the latter, shaking and incubation are carried out in all the steps. In the partial batch method according to the invention, by contrast, the mixtures are shaken, incubated and centrifuged (or the supernatant is removed from the chromatography material in some other way) in the equilibration and charging steps, but in the elution steps centrifuging is carried out immediately (or the supernatant is removed from the chromatography material in some other way). According to one embodiment of the invention, shaking and incubation are also carried out during the washing step while according to a second embodiment the washing buffer is carefully applied during the washing step and immediately eliminated by centrifuging or by some other method.

In order to be able to judge which method gives the best indications of suitable chromatography conditions, the above mentioned processes were tested on the purification of an antibody by hydrophobic interaction chromatography. Phenyl Sepharose 6 FF was used as the chromatography material. The antibody used binds when the conductivity of a 50 mM TRIS buffer of pH 6.5 is increased to 120 mS·cm$^{-1}$ with ammonium sulphate. Therefore, equilibration and washing buffers and the protein-containing charging solution were adjusted to these conditions. The elution buffer contained less ammonium sulphate and its conductivity was 50 mS·cm$^{-1}$. The incubation period for the equilibration was 5 minutes in each case, 21 minutes during charging and 9 minutes during washing, if applicable. The recovery rates in the fractions caught (run-through on charging: FT; Washing steps: W1 to W3, Elution steps: E1 to E4) are shown in Table 2.

As is clear from Table 2 the recovery rate for the partial batch method at 83.2% or 78.2% is substantially higher than in the batch method in which it was only possible to recover about two thirds of the material. Moreover, this experiment shows that in the batch method, particularly during the elution steps, the reproducibility is significantly worse than in the partial batch method (greater standard deviations). In this respect the partial batch method according to the embodiment with suspension during the washing step gives particularly good results. Reliable reproducibility of the results is an important prerequisite for the transferability of the optimum chromatography conditions thus determined to column chromatography process steps carried out on a larger scale.

Example 3

Use of the Process According to the Invention for Screening for Suitable Cation Exchanger Materials and Suitable Chromatography Conditions in the Purification of a Monoclonal Antibody In the preparation of antibodies in eukaryotic cell cultures the target protein typically occurs as a protein secreted into the medium in a complex mixture with other biomolecules. For the monoclonal antibody mAb1 the following screening was carried out in order to determine optimum conditions for the enrichment of the antibody using a cation exchanger:

Binding Screening:

Two screening runs were used to determine the optimum chromatography materials and the ideal binding conditions (Binding screening). The following chromatography materials were tested:

First run: SP Sepharose®, Toyopearl® SP 650 M, Toyopearl® SP 550 C, EMD Fractogel® SO3;

Second run: CM Ceramic Hyper DLS®, S Ceramic Hyper DF®, Poros 50 HS®, CM Sepharose FF.

SP and HS here stand for the sulphopropyl group as a functional group which is covalently coupled to the basic matrix of the chromatography material, SO3 represents the sulphoisobutyl group, CM denotes the carboxymethyl group and S denotes the sulphonic acid group.

The protein solutions used, i.e. the cell culture supernatants obtained after fermenting the expression cells by centrifugation and filtration, were adjusted to the conditions given in Table 3.1:

TABLE 2

| Fraction | FT | W1 | W2 | W3 | E1 | E2 | E3 | E4 | Total |
|---|---|---|---|---|---|---|---|---|---|
| Partial batch method/washing steps with suspension: | | | | | | | | | |
| Average value | 2.4% | 2.8% | 2.4% | 2.2% | 42.0% | 17.6% | 8.7% | 5.2% | 83.2% |
| Standard deviation | 0.7% | 0.4% | 0.4% | 0.3% | 1.9% | 0.8% | 0.4% | 0.2% | |
| Partial batch method/washing steps without suspension: | | | | | | | | | |
| Average value | 6.9% | 3.6% | 1.3% | 0.4% | 33.3% | 19.1% | 8.5% | 5.2% | 78.2% |
| Standard deviation | 4.0% | 1.5% | 0.4% | 0.1% | 3.1% | 1.5% | 1.0% | 0.7% | |
| Batch method: | | | | | | | | | |
| Average value | 2.2% | 2.8% | 2.0% | 1.5% | 30.2% | 16.4% | 7.7% | 3.8% | 66.5% |
| Standard deviation | 0.3% | 1.2% | 0.2% | 0.1% | 4.0% | 3.4% | 2.5% | 1.3% | |

TABLE 3.1

Conditions for the charging pools (Test solutions containing mAb1) in the first and second runs

|  | Pool 1 | Pool 2 | Pool 3 | Pool 4 | Pool 5 | Pool 6 | Pool 7 | Pool 8 |
|---|---|---|---|---|---|---|---|---|
| pH | 4.0 | 4.5 | 5.0 | 5.5 | 6.0 | 7.0 | 7.5 | 5.0 |
| Volume [ml] | 2.6 | 2.6 | 2.6 | 2.6 | 2.6 | 2.6 | 2.6 | 2.6 |
| Content [mg/ml] | 2.0 | 2.0 | 2.0 | 2.0 | 2.0 | 2.0 | 2.0 | 2.0 |

10% suspensions of the chromatography materials in 20% ethanol solution were used and 0.05 ml of gel bed were produced. The screening was carried out in the partial batch method described above (with suspension during the washing step). After two equilibration steps, charging with the protein solutions took place (test solutions containing mAb1; see Table 3.1) and a washing step. Elution was then carried out in three steps. The buffers were placed in two deep well plates (multi-well plates with a capacity of 2 ml; hereinafter also referred to as DWP) in accordance with the test arrangement described in Example 1, as specified in Tables 3.2 and 3.3. A triple measurement was made for each condition, and these measurements were compiled during the subsequent determination of the antibody concentrations by rProtA-HPLC (analytical affinity chromatography using recombinant protein A coupled to a basic matrix).

TABLE 3.2

Buffer conditions and arrangement on Deep Well Plate 1

| equilibration 1 (DWP1.1 column 1-4) | equilibration 2 (DWP1.2 column 5-8) | washing (DWP1.3 column 9-12) |
|---|---|---|
| | 50 mM acetate pH 4.0 | |
| | 50 mM acetate pH 4.5 | |
| | 50 mM acetate pH 5.0 | |
| | 50 mM phosphate pH 5.5 | |
| | 50 mM phosphate pH 6.0 | |
| | 50 mM Tris pH 6.5 | |
| | 50 mM Tris pH 7.0 | |
| | 50 mM acetate pH 5.0 | |

TABLE 3.3

Buffer conditions and arrangement on Deep Well Plate 2

| Elution 1 (DWP2.1 column 1-4) | Elution 2 (DWP2.2 column 5-8) | Elution 3 (DWP2.3 column 9-12) | pH |
|---|---|---|---|
| 50 mM Tris 0.3 M NaCl | 50 mM Tris 0.6 M NaCl | 50 mM Tris 1 M NaCl | pH 9.0 |

The mAB1 concentrations found in the run-throughs or eluates in the individual fractions are shown in FIGS. 3.1 to 3.8. On the basis of the retrieval, the SDS-PAGE analysis carried out with selected fractions and the binding characteristics, the following chromatography matrixes were selected for elution screening (Screening for optimum elution conditions): SP Sepharose® FF, Toyopearl® SP 650 M, Poros® 50 HS, EMD Fractogel® SO3.

Elution Screening:

In the elution screening the cell-free culture supernatants containing the mAb1 were adjusted to pH 5.0 and 6.5 as shown in Table 3.4:

TABLE 3.4

Conditions for the charging pools (test solutions containing mAb1) in the 1st and 2nd runs

|  | Pool 1 | Pool 2 | Pool 3 | Pool 4 | Pool 5 | Pool 6 | Pool 7 | Pool 8 |
|---|---|---|---|---|---|---|---|---|
| pH | 5.0 | 5.0 | 5.0 | 5.0 | 6.5 | 6.5 | 6.5 | 6.5 |
| volume [ml] | 2.6 | 2.6 | 2.6 | 2.6 | 2.6 | 2.6 | 2.6 | 2.6 |
| content [mg/ml] | 2.0 | 2.0 | 2.0 | 2.0 | 2.0 | 2.0 | 2.0 | 2.0 |

For the equilibration, washing and elution steps, the buffers listed in Tables 3.5 and 3.6 were added to the deep well plates:

TABLE 3.5

Buffer conditions and arrangement on Deep Well Plate 1

| equilibration 1 (DWP1.1 column 1-4) | equilibration 2 (DWP1.2 column 5-8) | washing (DWP1.3 column 9-12) |
|---|---|---|
| | 50 mM acetate pH 5.0 | |
| | 50 mM acetate pH 5.0 | |
| | 50 mM acetate pH 5.0 | |
| | 50 mM acetate pH 5.0 | |
| | 50 mM phosphate pH 6.5 | |
| | 50 mM phosphate pH 6.5 | |
| | 50 mM phosphate pH 6.5 | |
| | 50 mM phosphate pH 6.5 | |

TABLE 3.6

Buffer conditions and arrangement on Deep Well Plate 2

| Elution 1 (DWP2.1 column 1-4) | Elution 2 (DWP2.2 column 5-8) | Elution 3 (DWP2.3 column 9-12) | pH |
|---|---|---|---|
| 50 mM phosphate, 50 mM NaCl | + 100 mM NaCl | + 200 mM NaCl | 6.0 |
| 50 mM phosphate, 50 mM NaCl | + 100 mM NaCl | + 200 mM NaCl | 6.5 |
| 50 mM Tris, 50 mM NaCl | + 100 mM NaCl | + 200 mM NaCl | 7.0 |
| 50 mM Tris, 50 mM NaCl | + 100 mM NaCl | + 200 mM NaCl | 7.5 |
| 50 mM phosphate, 50 mM NaCl | + 100 mM NaCl | + 200 mM NaCl | 6.0 |
| 50 mM phosphate, | + 100 mM NaCl | + 200 mM NaCl | 6.5 |

TABLE 3.6-continued

Buffer conditions and arrangement on Deep Well Plate 2

| Elution 1 (DWP2.1 column 1-4) | Elution 2 (DWP2.2 column 5-8) | Elution 3 (DWP2.3 column 9-12) | pH |
|---|---|---|---|
| 50 mM NaCl 50 mM Tris, 50 mM NaCl | + 100 mM NaCl | + 200 mM NaCl | 7.0 |
| 50 mM Tris, 50 mM NaCl | + 100 mM NaCl | + 200 mM NaCl | 7.5 |

FIGS. 3.9 to 3.12 show, in graph form, the percentage amounts of the total quantity of mAb1 applied per well in the individual steps under the condition specified. With respect to the retrieval rate of the target protein and advantageously low salt concentrations (which it is desirable to minimise with a view to the costs of transfer to an industrial scale, for example) charging at pH 5 and elution at pH 6.5 and 0.05 M salt on EMD Fractogel® SO3 were identified as suitable conditions (see FIG. 3.12, B10-B12).

Example 4

Possibility of Correlating the Results of the Screening Method According to the Invention in Micro-Well Filter Plates with the Results of Conventional Column Experiments Using the optimum conditions determined in Example 3, column chromatography experiments were carried out with 1 ml of bed volume. The flow was 0.5 ml/min. The charging of the column was carried out with a salt concentration of 0 M NaCl at pH 5. The washing step was carried out under the same conditions. For elution, a stepped gradient of 0/0.05/0.1/0.2 M NaCl was used. This imitates the conditions of the screen in the micro-well filter plate in which EMD Fractogel® SO3 was used and the binding step at pH 5 and elution steps at pH 6.5 were carried out.

Figure 4:
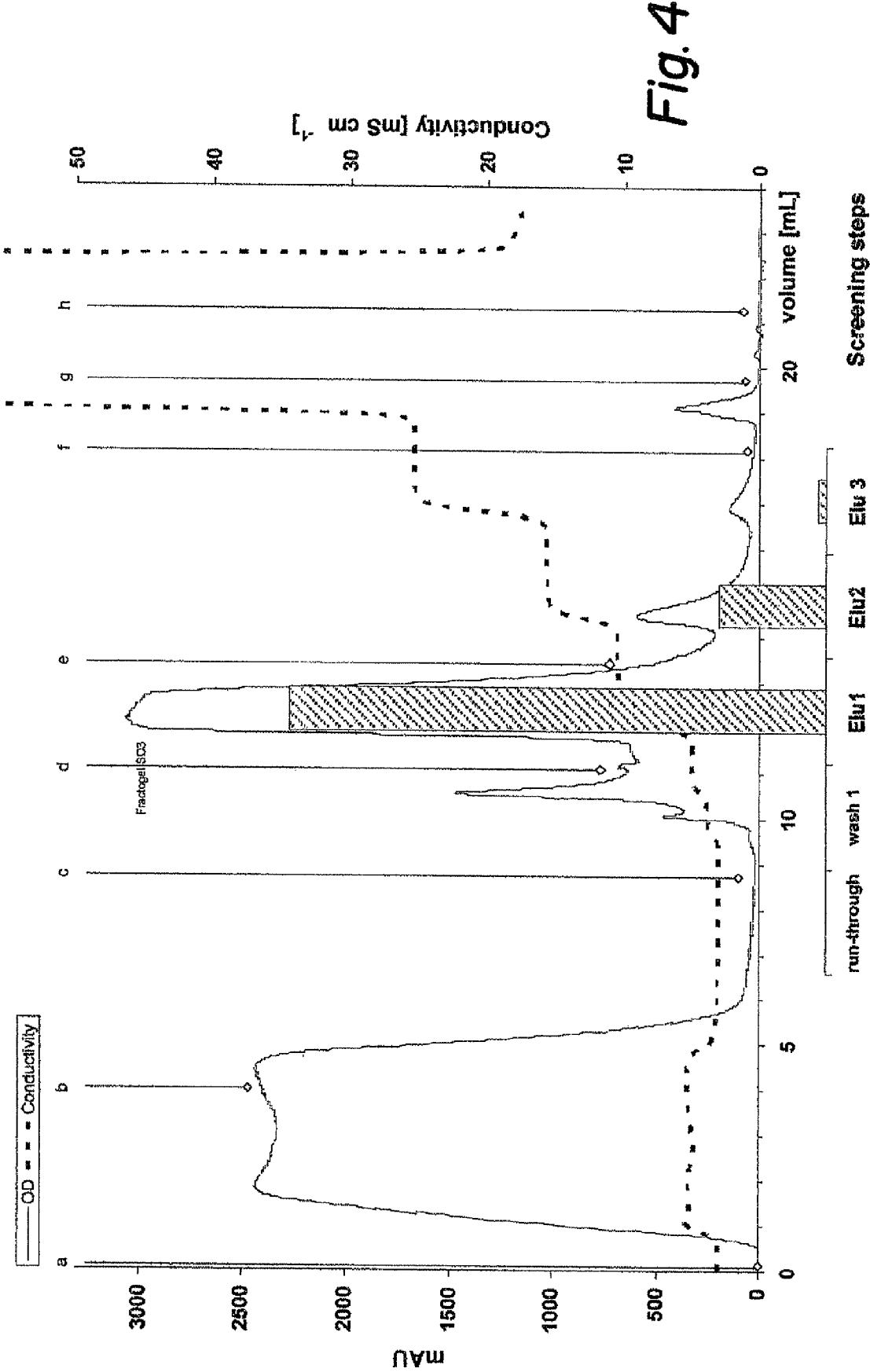
FIG. 4 shows by comparison the elution profile, obtained in Example 4, for a column-chromatographic purification of the protein mAb1 (solid line: protein concentration; broken line: conductivity) and the mAb1 concentration in a screen in multi-well filter plates under corresponding conditions (bars).

In FIG. 4 the elution profile of the column chromatography carried out in the above manner (solid line: protein concentration; broken line: conductivity) and the percentage amounts of the total quantity of mAb1 applied per well, as obtained in the screening according to the invention in multi-well filter plates under the corresponding conditions in Example 3 (bars), are superimposed. Further analysis of the run-throughs and eluates by SDS-PAGE was able to demonstrate that the distribution of the mAb1 product in the peaks coincides with that in the screening, i.e. enriched mAb1 was present in the corresponding eluates. This demonstrates the transferability of the optimised chromatography conditions discovered by the process according to the invention to methods in which chromatography columns are used.

Example 5

Screening for the Behaviour of a Monoclonal Antibody on Hydrophobic Interaction Matrices Under Different Chromatography Conditions For this example, an antibody mAb2 enriched by rProteinA affinity chromatography in a first step was used. The purpose of the screenings was to determine the behaviour of mAb2 in response to hydrophobic interaction matrices as chromatography materials, in order to decide whether in a next step binding or through-flow conditions with respect to the antibody mAb2 should be investigated, i.e. whether a further purification effect can be achieved by causing the antibody to bind to the column and allow impurities to run through as far as possible, or to allow the antibody to run through and enrich the impurities by binding them to the column material.

The following chromatography materials were used: Phenyl Sepharose® HP, Phenyl Sepharose® FF, Toyopearl® Phenyl and Toyopearl® Butyl. The protein solutions used were adjusted to the conditions specified in Table 5.1:

TABLE 5.1

Conditions for the charging pools (test solutions containing mAb2) in the 1st and 2nd runs

| | Pool 1 | Pool 2 | Pool 3 | Pool 4 | Pool 5 | Pool 6 | Pool 7 | Pool 8 |
|---|---|---|---|---|---|---|---|---|
| pH | 6.5 | 6.5 | 6.5 | 6.5 | 6.5 | 6.5 | 6.5 | 6.5 |
| ammonium sulphate (AS) | 0 M | 0.1 M | 0.26 M | 0.3 M | 0.4 M | 0.6 M | 0.8 M | 1 M |
| volume [ml] | 2.6 | 2.6 | 2.6 | 2.6 | 2.6 | 2.6 | 2.6 | 2.6 |
| content [mg/ml] | 1.64 | 1.64 | 1.64 | 1.64 | 1.64 | 1.64 | 1.64 | 1.64 |

10% suspensions of the chromatography materials in 20% ethanol solution were used and in this way a gel bed of 0.05 ml was produced. The partial batch method was used. As in Example 3, after two equilibration steps, charging with protein-containing test solutions was carried out (see Table 5.1) followed by a washing step (with suspension of the chromatography material). Elution was then carried out in three steps. The buffers were placed in two deep well plates according to the test arrangement described in Example 1, as shown in Tables 5.2 and 5.3. A triple measurement was made of each condition. As there were only a few impurities present in the protein solution used for the screening, the product concentration could subsequently be determined by absorption at 280 nm in a microtitre plate photometer.

TABLE 5.2

Buffer conditions and arrangement on Deep Well Plate 1

| equilibration 1 (DWP1.1 column 1-4) | equilibration 2 (DWP1.2 column 5-8) | washing (DWP1.3 column 9-12) | pH |
|---|---|---|---|
| 50 mM Tris 0 M AS | 50 mM Tris 0 M AS | 50 mM Tris 0 M AS | pH 6.5 |
| 50 mM Tris, 0.1 M AS | 50 mM Tris, 0.1 M AS | 50 mM Tris, 0.1 M AS | |
| 50 mM Tris, 0.2 M AS | 50 mM Tris, 0.2 M AS | 50 mM Tris, 0.2 M AS | |
| 50 mM Tris, 0.3 M AS | 50 mM Tris, 0.3 M AS | 50 mM Tris, 0.3 M AS | |
| 50 mM Tris 0.4 M AS | 50 mM Tris 0.4 M AS | 50 mM Tris 0.4 M AS | |
| 50 mM Tris, 0.6 M AS | 50 mM Tris, 0.6 M AS | 50 mM Tris, 0.6 M AS | |
| 50 mM Tris, 0.8 M AS | 50 mM Tris, 0.8 M AS | 50 mM Tris, 0.8 M AS | |
| 50 mM Tris, 1 M AS | 50 mM Tris, 1 M AS | 50 mM Tris, 1 M AS | |

TABLE 5.3

Buffer conditions and arrangement on Deep Weil Plate 2

| Elution 1 (DWP2.1 column 1-4) | Elution 2 (DWP2.2 column 5-8) | Elution 3 (DWP2.3 column 9-12) | pH |
|---|---|---|---|
| 50 mM Tris 0 M AS | 50 mM Tris 0 M AS | 50 mM Tris 0 M AS | pH 6.5 |
| 50 mM Tris, 0 M AS | 50 mM Tris, 0 M AS | 50 mM Tris, 0 M AS | |
| 50 mM Tris, 0.1 M AS | 50 mM Tris, 0 M AS | 50 mM Tris, 0 M AS | |
| 50 mM Tris, 0.2 AS | 50 mM Tris, 0.1 AS | 50 mM Tris 0 M AS | |
| 50 mM Tris 0.2 M AS | 50 mM Tris 0.1 M AS | 50 mM Tris, 0 M AS | |
| 50 mM Tris, 0.4 M AS | 50 mM Tris, 0.2 M AS | 50 mM Tris, 0 M AS | |
| 50 mM Tris, 0.6 M AS | 50 mM Tris, 0.3 M AS | 50 mM Tris, 0 M AS | |
| 50 mM Tris, 0.6 M AS | 50 mM Tris, 0.3 M AS | 50 mM Tris, 0 M AS | |

The product concentrations in the individual fractions are shown in FIGS. 5.1 to 5.4. It was found that mAb2 binds to the hydrophobic matrix only at very high salt concentrations. Thus in the case of mAb2 it is more favourable to construct a hydrophobic interaction chromatography process step as a throughflow chromatography step. The optimum conditions for this can be determined easily and at low cost by further screens carried out using the method according to the invention.

The invention claimed is:

1. A method of finding suitable parameters for chromatographic processes for separating biomolecules,
    wherein tests comprising a sequence of equilibration, charging, washing and elution steps are carried out on a small scale, with variation of individual parameters, and from the results of these tests conclusions are drawn as to optimum parameters, characterised in that the sequence of equilibration, charging, washing and elution steps is carried out by the partial batch method (steps with and without suspension of the chromatography material), wherein at least the charging step comprises suspending the chromatography material and at least during an elution step there is no suspension of the chromatography material, wherein
    (a) a suspension of a chromatography material is placed in a plurality of wells in a multi-well filter plate,
    (b) a moist gel bed is produced in the wells containing the suspension, by removing the supernatant above the chromatography material by centrifugation or by the application of a pressure differential,
    (c) in order to equilibrate the chromatography material contained in the wells an equilibrating buffer solution is added to the moist gel bed and the gel bed is suspended (equilibration step),
    (d) a moist gel bed is produced according to step (b),
    (e) optionally steps (c) and (d) are repeated several times, in particular once, twice or three times,
    (f) in order to charge the chromatography material a test solution containing at least one biomolecule is added to the gel bed, and the gel bed is suspended (charging step),
    (g) a moist gel bed is produced according to step (b),
    (h) in order to wash the chromatography material a washing solution is added to the gel bed, the gel bed optionally being suspended (washing step),
    (i) a moist gel bed is produced according to step (b),
    (k) optionally steps (h) and (i) are repeated several times, particularly once, twice or three times, while the washing solutions used may have the same or different compositions and optionally the gel bed is suspended or is not suspended,
    (l) for eluting the biomolecule, an eluting solution is added to the gel bed without causing suspension of the gel bed (elution step),
    (m) according to step (b) a moist gel bed is produced and the eluate is caught,
    (n) optionally steps (l) and (m) are repeated several times, particularly once, twice or three times, while the eluant solutions used may have the same or different compositions, and
    (o) the eluates collected are analysed.

2. The method according to claim 1, wherein the equilibration, charging, washing and elution steps are carried out in a number of parallel tests, wherein the chromatography conditions differ in at least two of the tests and by comparing the chromatography results of the respective experiments conclusions are drawn as to advantageous chromatography conditions.

3. The method according to claim 2, wherein the equilibration, charging, washing and elution steps are carried out in parallel tests on a multi-well filter plate.

4. The method according to claim 1, wherein one or more steps are carried out using a pipetting robot.

5. The method according to claim 1, wherein a material for ion exchange, hydrophobic interaction, affinity, hydroxy apatite, reversed phase, hydrophobic charge induction or mixed mode chromatography is used as the chromatography material.

6. The method according to claim 1, wherein the suspension is effected by shaking the chromatography material or by pipetting the chromatography material on or off.

7. The method according to claim 1, wherein the biomolecule is a protein, a protein mixture or a mixture of host cell proteins and an over-expressed target protein.

8. The method according to claim 1, wherein said equilibration, charging, washing and elution steps comprise adding an equilibrating solution and/or a test solution and/or a washing solution and/or an eluting solution, wherein after the addition of the equilibrating solution and/or the test solution and/or the washing solution and/or the eluting solution the chromatography material is incubated with the equilibration, testing, washing or elution solution.

9. The method according to claim 1, wherein the eluates of the elution step or steps and optionally also the run-throughs from the charging and washing steps are recovered and analysed.

10. The method according to claim 1, wherein the chromatography material for each mixture is used in an amount such that the gel bed thus obtained has a volume of between 0.01 ml and 2 ml.

11. The method according to claim 1, wherein the chromatography material is in a multi-well filter plate and the suspension is effected by shaking the multi-well filter plate.

* * * * *

UNITED STATES PATENT AND TRADEMARK OFFICE
CERTIFICATE OF CORRECTION

| | | |
|---|---|---|
| PATENT NO. | : 8,349,615 B2 | Page 1 of 1 |
| APPLICATION NO. | : 11/762119 | |
| DATED | : January 8, 2013 | |
| INVENTOR(S) | : Christian Eckermann | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1064 days.

Signed and Sealed this
Eleventh Day of November, 2014

Michelle K. Lee
*Deputy Director of the United States Patent and Trademark Office*